United States Patent
Wang et al.

(10) Patent No.: US 7,345,046 B2
(45) Date of Patent: Mar. 18, 2008

(54) HETEROARYL-FUSED PYRIMIDINYL COMPOUNDS AS ANTICANCER AGENTS

(75) Inventors: Weibo Wang, Moraga, CA (US); Liana Marie Lagniton, Berkeley, CA (US); Ryan N. Constantine, Oakland, CA (US); Matthew T. Burger, Albany, CA (US)

(73) Assignee: Chiron Corporation, Emeryville, CA (US)

( * ) Notice: Subject to any disclaimer, the term of this patent is extended or adjusted under 35 U.S.C. 154(b) by 228 days.

(21) Appl. No.: 10/850,429

(22) Filed: May 21, 2004

(65) Prior Publication Data

US 2005/0065169 A1    Mar. 24, 2005

Related U.S. Application Data

(60) Provisional application No. 60/474,684, filed on May 30, 2003.

(51) Int. Cl.
| | |
|---|---|
| A61K 31/519 | (2006.01) |
| A61K 31/13 | (2006.01) |
| A61K 33/24 | (2006.01) |
| A61K 33/42 | (2006.01) |
| A61K 39/395 | (2006.01) |
| A61K 31/337 | (2006.01) |
| A61K 31/497 | (2006.01) |
| A61K 31/436 | (2006.01) |
| A61K 31/506 | (2006.01) |
| A61K 31/555 | (2006.01) |
| C07D 495/04 | (2006.01) |
| A61P 35/04 | (2006.01) |

(52) U.S. Cl. .......... 514/260.1; 544/278; 435/810; 514/283; 514/90; 514/274; 514/186; 514/252.16; 514/252.18; 514/475; 424/144.1; 424/142.1; 424/649; 424/770

(58) Field of Classification Search ............ 544/278; 514/260.1

See application file for complete search history.

(56) References Cited

FOREIGN PATENT DOCUMENTS

| WO | WO 01/98278 | 12/2001 |
|---|---|---|
| WO | WO 02/083143 | 10/2002 |
| WO | WO 03/039460 | 5/2003 |
| WO | WO 03/049527 | 6/2003 |
| WO | WO 03/049679 | 6/2003 |
| WO | WO 03/050064 | 6/2003 |
| WO | WO 03/050122 | 6/2003 |
| WO | WO 03/103575 | 12/2003 |
| WO | WO 2004/034972 | 4/2004 |
| WO | WO 2004/039774 | 5/2004 |

OTHER PUBLICATIONS

Coleman, P.J.; Fraley, M. E.; Expert. Opin. Ther. Patents; 2004; 14(12); 1659-1667.*
Yan et al, "Inhibition of a Mitotic Motor Protein: Where, How, and Conformational Consequences" *J. Mol. Biol.* 335:547-554, 2004.

* cited by examiner

*Primary Examiner*—Brenda L. Coleman
*Assistant Examiner*—Susanna Moore
(74) *Attorney, Agent, or Firm*—George Renzoni; Susan L. Abrahamson; Alisa A. Harbin

(57) ABSTRACT

Heteroaryl-fused pyrimidinyl compounds, pharmaceutically acceptable salts, and prodrugs thereof; compositions that include a pharmaceutically acceptable carrier and one or more of the heteroaryl-fused pyrimidinyl compounds, either alone or in combination with at least one additional therapeutic agent. Methods of using the heteroaryl-fused pyrimidinyl compounds, either alone or in combination with at least one additional therapeutic agent, in the prophylaxis or treatment of proliferative diseases.

40 Claims, No Drawings

HETEROARYL-FUSED PYRIMIDINYL COMPOUNDS AS ANTICANCER AGENTS

CROSS-REFERENCES TO RELATED APPLICATIONS

This application claims the benefit of U.S. Provisional Application No. 60/474,684, filed May 30, 2003.

FIELD OF THE INVENTION

The present invention relates to new heteroaryl-fused pyrimidinyl compounds, their pharmaceutically acceptable salts, and prodrugs thereof; compositions of the new compounds, either alone or in combination with at least one additional therapeutic agent, with a pharmaceutically acceptable carrier; and uses of the new compounds, either alone or in combination with at least one additional therapeutic agent, in the prophylaxis or treatment of proliferative diseases.

BACKGROUND OF THE INVENTION

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmatic reticulum. Several KRPs interact with the microtubules of the mitotic spindle or with the chromosomes directly, and appear to play a pivotal role during the mitotic stages of the cell cycle. These mitotic KRPs are of particular interest for the development of cancer therapeutics.

KSP (also known as Eg5, HsKSP kinesin, KNSL1,) is one of several kinesin-like motor proteins that are localized to the mitotic spindle and known to be required for formation and/or function of the bipolar mitotic spindle.

In 1995, the depletion of KSP kinesin using an antibody directed against the C-terminus of KSP was shown to arrest HeLa cells in mitosis with monoastral microtubule arrays (Blangy et al., *Cell* 83:1159-1169, 1995). Mutations in bimC and cut7 genes, which are considered to be homologues of KSP kinesin, cause failure in centrosome separation in *Aspergillus nidulans* (Enos, A. P., and N. R. Morris, *Cell* 60:1019-1027, 1990) and *Schizosaccharomyces pombe* (Hagan, I., and M. Yanagida, *Nature* 347:563-566, 1990). Treatment of cells with either ATRA (all trans-retinoic acid), which reduces HsKSP kinesin expression on protein level, or depletion of HsKSP kinesin using antisense oligonucleotides revealed a significant growth inhibition in DAN-G pancreatic carcinoma cells indicating that HsKSP kinesin might be involved in the antiproliferative action of all trans-retinoic acid (Kaiser, A., et al., *J. Biol. Chem.* 274, 18925-18931, 1999). Interestingly, the *Xenopus laevis* Aurora-related protein kinase pEg2 was shown to associate and phosphorylate XlKSP kinesin (Giet, R., et al., *J. Biol. Chem.* 274:15005-15013, 1999). Potential substrates of Aurora-related kinases are of particular interest for cancer drug development. For example, Aurora 1 and 2 kinases are overexpressed on protein and RNA level and the genes are amplified in colon cancer patients.

The first cell permeable small molecule inhibitor for HsKSP kinesin, "monastrol", was shown to arrest cells with monopolar spindles without affecting microtubule polymerization as do conventional chemotherapeutics such as taxanes and vinca alkaloids (Mayer, T. U., et al., *Science* 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., *Biochemistry* 42:338-349, 2003; Kapoor, T. M., et al., *J. Cell Biol.* 150:975-988, 2000).

Recently, other KSP kinesin inhibitors have been described. WO 02/057244 and WO 02/056880 describe phenothiazine compounds and triphenylmethane compounds, respectively, for treating proliferative diseases. WO 02/078639 describes cyano-substituted dihydropyrimidine compounds for treating proliferative diseases. U.S. Pat. No. 6,472,521 describes oligonucleotides and oligonucleotide derivatives for inhibiting human KSP expression.

WO 01/98278, WO 01/30768, and WO 03/039460 describe quinazolinone compounds that are useful in treating cellular proliferative diseases associated with KSP kinesin activity. The compounds described in these references are 2-(2-aminomethyl)quinazolinone derivatives. The quinazolinone compounds described in WO 01/98278 and WO 01/30768 have 2-aminomethyl substituents that are either amine, amide, or sulfonamide substituents. The quinazolinone compounds described in WO 03/039460 have the amino group of the 2-aminomethyl substituent incorporated into a 5-12 membered nitrogen-containing heterocycle.

WO 03/050064 describes thienopyrimidinone compounds that are useful for treating cellular proliferative disease, for treating disorders associated with KSP kinesin activity, and for inhibiting KSP kinesin.

WO 03/103575 describes heterocyclic-fused pyrimidinone derivatives that are inhibitors of the mitotic kinesin KSP and that are useful in the treatment of cellular proliferative diseases. These derivatives are N-heterocyclic-fused pyrimidinone derivatives. Representative derivatives that are described include pyrido[α,β-γ]pyrimidin-δ-ones, pyrimido[α,β-γ]pyrimidin-δ-ones, pyrimido[α,β-γ]pyridazin-δ-ones, and pteridin-4-ones.

SUMMARY OF THE INVENTION

In one aspect of the present invention, new heteroaryl-fused pyrimidinyl compounds, their pharmaceutically acceptable salts, and prodrugs thereof are provided. The heteroaryl-fused pyrimidinyl compounds, pharmaceutically acceptable salts, and prodrugs are KSP inhibitors and are useful in the treating cellular proliferation diseases.

In one embodiment, the heteroaryl-fused pyrimidinyl compounds have the formula (I):

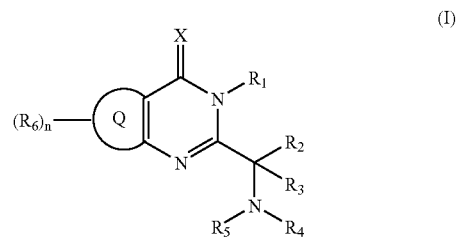

wherein Q is heteroaryl;

X is O or S;

R$_1$ is hydrogen, or substituted or unsubstituted alkyl, alkenyl, alkynyl, aryl, heteroaryl, heterocyclyl, alkylsulfonyl, or arylsulfonyl;

R$_2$ is hydrogen, or substituted or unsubstituted alkyl, alkenyl, alkynyl, aryl, heteroaryl, heterocyclyl, alkylsulfonyl, arylsulfonyl, alkylcarboxy, aminocarboxy, aminocarbonyl, or alkylsulfonamido; or COR$_7$, CO$_2$R$_7$, CONR$_8$R$_9$, S(O)$_m$R$_{10}$, or SO$_2$NR$_{11}$R$_{12}$;

R$_3$ is cyano, substituted or unsubstituted arylsulfonyl, or CONR$_8$R$_9$;

R$_4$ is hydrogen, or substituted or unsubstituted alkyl, alkenyl, alkynyl, aryl, heteroaryl, or heterocyclyl; or L-R$_{13}$, wherein L is a C1-C10 saturated or unsaturated branched or unbranched carbon chain comprising one or more methylene groups, wherein one or more methylene groups are optionally independently replaced by O, N, or S; and wherein L is optionally substituted with one or two oxo groups and one or more C1-C10 branched or unbranched alkyl optionally substituted by one or more halogen atoms;

R$_5$ is hydrogen, or substituted or unsubstituted alkyl, alkenyl, alkynyl, alkoxy, aryl, heteroaryl, or heterocyclyl; or COR$_7$, CO$_2$R$_7$, CONR$_8$R$_9$, or SO$_{(m)}$R$_{10}$;

R$_6$ is hydrogen, halogen, hydroxy, nitro, amino, cyano, alkoxy, alkylthio, methylenedioxy, or haloalkoxy; or substituted or unsubstituted alkyl, alkenyl, alkynyl, aryl, heteroaryl, alkylamino, dialkylamino, alkylsulfonyl, arylsulfonyl, alkylcarboxy, carboxyamino, carboxyamido, aminocarboxy, aminocarbonyl, or alkylsulfonamido;

R$_7$, R$_8$, R$_9$, R$_{10}$, R$_{11}$, and R$_{12}$ are independently selected from hydrogen, or substituted or unsubstituted alkyl, alkenyl, alkynyl, aryl, heteroaryl, or heterocyclyl; or R$_8$ and R$_9$, or R$_{11}$ and R$_{12}$ taken together form a 3- to 7-membered carbocyclic or heterocyclic ring;

R$_{13}$ is amino, alkylamino, or dialkylamino; or substituted or unsubstituted guanidino or heterocyclyl;

m=0, 1, or 2; and n=0, 1, 2, or 3; or the tautomers, pharmaceutically acceptable salts, or prodrugs thereof.

In another embodiment, the heteroaryl-fused pyrimidinyl compounds have the formula (II):

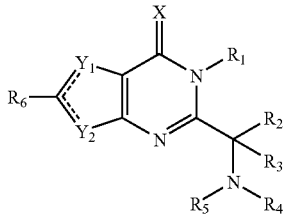

(II)

wherein X is O or S;

Y$_1$ is S, O, or NR$_{14}$ and Y$_2$ is CR$_{15}$; or
Y$_1$ is CR$_{15}$ and Y$_2$ is S, O, or NR$_{14}$; or
Y$_1$ is N and Y$_2$ is S, O, or NR$_{14}$; or
Y$_1$ is S, O, NR$_{14}$ and Y$_2$ is N;

wherein, the dashed line represents a double bond to Y$_1$, when Y$_1$ is CR$_{15}$ or N, and a double bond to Y$_2$, when Y$_2$ is CR$_{15}$ or N;

R$_1$ is hydrogen, or substituted or unsubstituted alkyl, alkenyl, alkynyl, aryl, heteroaryl, heterocyclyl, alkylsulfonyl, or arylsulfonyl;

R$_2$ is hydrogen, or substituted or unsubstituted alkyl, alkenyl, alkynyl, aryl, heteroaryl, heterocyclyl, alkylsulfonyl, arylsulfonyl, alkylcarboxy, aminocarboxy, aminocarbonyl, or alkylsulfonamido; or COR$_7$, CO$_2$R$_7$, CONR$_8$R$_9$, S(O)$_m$R$_{10}$, or S$_2$NR$_{11}$R$_{12}$;

R$_3$ is cyano, substituted or unsubstituted arylsulfonyl, or CONR$_8$R$_9$;

R$_4$ is hydrogen, or substituted or unsubstituted alkyl, alkenyl, alkynyl, aryl, heteroaryl, or heterocyclyl; or L-R$_{13}$, wherein L is a C1-C10 saturated or unsaturated branched or unbranched carbon chain comprising one or more methylene groups, wherein one or more methylene groups are optionally independently replaced by O, N, or S; and wherein L is optionally substituted with one or two oxo groups and one or more C1-C10 branched or unbranched alkyl optionally substituted by one or more halogen atoms;

R$_5$ is hydrogen, or substituted or unsubstituted alkyl, alkenyl, alkynyl, alkoxy, aryl, heteroaryl, or heterocyclyl; or COR$_7$, CO$_2$R$_7$, CONR$_8$R$_9$, or SO$_{(m)}$R$_{10}$;

R$_6$ is hydrogen, halogen, hydroxy, nitro, amino, cyano, alkoxy, alkylthio, methylenedioxy, or haloalkoxy; or substituted or unsubstituted alkyl, alkenyl, alkynyl, aryl, heteroaryl, alkylamino, dialkylamino, alkylsulfonyl, arylsulfonyl, alkylcarboxy, carboxyamino, carboxyamido, aminocarboxy, aminocarbonyl, or alkylsulfonamido;

R$_7$, R$_8$, R$_9$, R$_{10}$, R$_{11}$, and R$_{12}$ are independently selected from hydrogen, or substituted or unsubstituted alkyl, alkenyl, alkynyl, aryl, heteroaryl, or heterocyclyl; or R$_8$ and R$_9$, or R$_{11}$ and R$_{12}$ taken together form a 3- to 7-membered carbocyclic or heterocyclic ring;

R$_{13}$ is amino, alkylamino, or dialkylamino; or substituted or unsubstituted guanidino or heterocyclyl;

R$_{14}$ and R$_{15}$ are independently selected from hydrogen, or substituted or unsubstituted alkyl, alkenyl, alkynyl, aryl, heteroaryl, or heterocyclyl;

m=0, 1, or 2; or the tautomers, pharmaceutically acceptable salts, or prodrugs thereof.

In another embodiment, the heteroaryl-fused pyrimidinyl compounds have the formula (III):

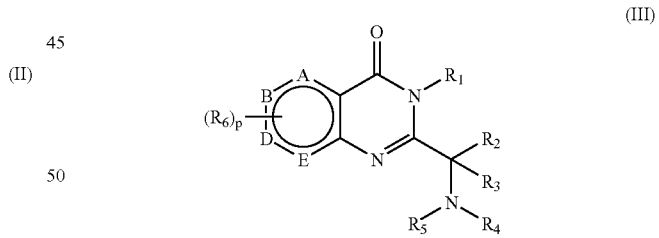

(III)

wherein, A, B, D, and E are independently selected from N, CH, or CR$_6$, with the proviso that at least one, but no more than two of A, B, D, or E are N;

R$_1$ is hydrogen, or substituted or unsubstituted alkyl, alkenyl, alkynyl, aryl, heteroaryl, heterocyclyl, alkylsulfonyl, or arylsulfonyl;

R$_2$ is hydrogen, or substituted or unsubstituted alkyl, alkenyl, alkynyl, aryl, heteroaryl, heterocyclyl, alkylsulfonyl, arylsulfonyl, alkylcarboxy, aminocarboxy, aminocarbonyl, or alkylsulfonamido; or COR$_7$, CO$_2$R$_7$, CONR$_8$R$_9$, S(O)$_m$R$_{10}$, or SO$_2$NR$_{11}$R$_{12}$;

R$_3$ is cyano, substituted or unsubstituted arylsulfonyl, or CONR$_8$R$_9$;

$R_4$ is hydrogen, or substituted or unsubstituted alkyl, alkenyl, alkynyl, aryl, heteroaryl, or heterocyclyl; or L-$R_{13}$, wherein L is a C1-C10 saturated or unsaturated branched or unbranched carbon chain comprising one or more methylene groups, wherein one or more methylene groups are optionally independently replaced by O, N, or S; and wherein L is optionally substituted with one or two oxo groups and one or more C1-C10 branched or unbranched alkyl optionally substituted by one or more halogen atoms;

$R_5$ is hydrogen, or substituted or unsubstituted alkyl, alkenyl, alkynyl, alkoxy, aryl, heteroaryl, or heterocyclyl; or $COR_7$, $CO_2R_7$, $CONR_8R_9$, or $SO_{(m)}R_{10}$;

$R_6$ is hydrogen, halogen, hydroxy, nitro, amino, cyano, alkoxy, alkylthio, methylenedioxy, or haloalkoxy; or substituted or unsubstituted alkyl, alkenyl, alkynyl, aryl, heteroaryl, alkylamino, dialkylamino, alkylsulfonyl, arylsulfonyl, alkylcarboxy, carboxyamino, carboxyamido, aminocarboxy, aminocarbonyl, or alkylsulfonamido;

$R_7$, $R_8$, $R_9$, $R_{10}$, $R_{11}$, and $R_{12}$ are independently selected from hydrogen, or substituted or unsubstituted alkyl, alkenyl, alkynyl, aryl, heteroaryl, or heterocyclyl; or $R_8$ and $R_9$, or $R_{11}$ and $R_{12}$ taken together form a 3- to 7-membered carbocyclic or heterocyclic ring;

$R_{13}$ is amino, alkylamino, or dialkylamino; or substituted or unsubstituted guanidino or heterocyclyl;

m=0, 1, or 2; and p=0, 1, 2, or 3; or the tautomers, pharmaceutically acceptable salts, or prodrugs thereof.

In another aspect, the present invention provides methods for treating proliferative diseases in a human or animal subject in need of such treatment comprising administering to said subject an amount of a compound of formula (I), (II), or (III) effective to reduce or prevent cellular proliferation in the subject.

In another aspect, the present invention provides methods for treating proliferative diseases in a human or animal subject in need of such treatment, comprising administering to said subject an amount of a compound of formula (I), (II), or (III) effective to reduce or prevent cellular proliferation in the subject in combination with at least one additional agent for the treatment of cancer.

In other aspects, the present invention provides therapeutic compositions, comprising at least one compound of formula (I), (II), or (III) in combination with one or more additional agents for the treatment of cancer, as are commonly employed in cancer therapy.

The compounds of the invention are useful in the treatment of cancers, including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

The invention further provides compositions, kits, methods of use, and methods of manufacture as described in the detailed description of the invention.

DETAILED DESCRIPTION OF THE PREFERRED EMBODIMENT

In one aspect of the present invention, new heteroaryl-fused pyrimidinyl compounds, their pharmaceutically acceptable salts, and prodrugs thereof are provided. The heteroaryl-fused pyrimidinyl compounds, pharmaceutically acceptable salts, and prodrugs are KSP inhibitors and are useful in the treating cellular proliferation diseases.

In one embodiment, the heteroaryl-fused pyrimidinyl compounds have the formula (I):

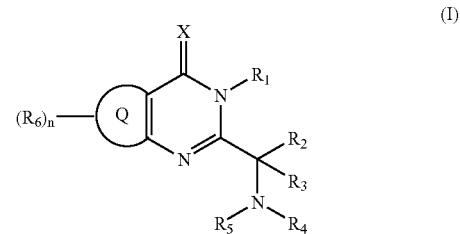

(I)

wherein Q is heteroaryl;

X is O or S;

$R_1$ is hydrogen, or substituted or unsubstituted alkyl, alkenyl, alkynyl, aryl, heteroaryl, heterocyclyl, alkylsulfonyl, or arylsulfonyl;

$R_2$ is hydrogen, or substituted or unsubstituted alkyl, alkenyl, alkynyl, aryl, heteroaryl, heterocyclyl, alkylsulfonyl, arylsulfonyl, alkylcarboxy, aminocarboxy, aminocarbonyl, or alkylsulfonamido; or $COR_7$, $CO_2R_7$, $CONR_8R_9$, $S(O)_mR_{10}$, or $SO_2NR_{11}R_{12}$;

$R_3$ is cyano, substituted or unsubstituted arylsulfonyl, or $CONR_8R_9$;

$R_4$ is hydrogen, or substituted or unsubstituted alkyl, alkenyl, alkynyl, aryl, heteroaryl, or heterocyclyl; or L-$R_{13}$, wherein L is a C1-C10 saturated or unsaturated branched or unbranched carbon chain comprising one or more methylene groups, wherein one or more methylene groups are optionally independently replaced by O, N, or S; and wherein L is optionally substituted with one or two oxo groups and one or more C1-C10 branched or unbranched alkyl optionally substituted by one or more halogen atoms;

$R_5$ is hydrogen, or substituted or unsubstituted alkyl, alkenyl, alkynyl, alkoxy, aryl, heteroaryl, or heterocyclyl; or $COR_7$, $CO_2R_7$, $CONR_8R_9$, or $SO_{(m)}R_{10}$;

$R_6$ is hydrogen, halogen, hydroxy, nitro, amino, cyano, alkoxy, alkylthio, methylenedioxy, or haloalkoxy; or substituted or unsubstituted alkyl, alkenyl, alkynyl, aryl, heteroaryl, alkylamino, dialkylamino, alkylsulfonyl, arylsulfonyl, alkylcarboxy, carboxyamino, carboxyamido, aminocarboxy, aminocarbonyl, or alkylsulfonamido;

$R_7$, $R_8$, $R_9$, $R_{10}$, $R_{11}$, and $R_{12}$ are independently selected from hydrogen, or substituted or unsubstituted alkyl, alkenyl, alkynyl, aryl, heteroaryl, or heterocyclyl; or $R_8$ and $R_9$, or $R_{11}$ and $R_{12}$ taken together form a 3- to 7-membered carbocyclic or heterocyclic ring;

$R_{13}$ is amino, alkylamino, or dialkylamino; or substituted or unsubstituted guanidino or heterocyclyl;

m=0, 1, or 2; and n=0, 1, 2, or 3; or the tautomers, pharmaceutically acceptable salts, or prodrugs thereof.

Suitable Q groups include thienyl, thiazolyl, imidazolyl, pyrazolyl, pyridyl, pyridazinyl, piperazinyl, azetidinyl, triazolyl, benzimidazolyl, benzothiazolyl, and benzoxazolyl groups. In one embodiment, Q is thienyl. In another embodiment, Q is pyridyl.

Suitable substituted alkyl groups include arylalkyl, heteroarylalkyl, heterocyclyalkyl, aminoalkyl, alkylaminoalkyl, dialkyaminoalkyl, and sulfonamidoalkyl groups.

In one embodiment, X is O.

In one embodiment, $R_1$ is arylalkyl. In one embodiment, the arylalkyl is benzyl.

In one embodiment, $R_2$ is hydrogen and $R_3$ is $CONR_8R_9$. In one embodiment, $R_8$ and $R_9$ are independently selected from hydrogen, methyl, ethyl, or isopropyl.

In one embodiment, $R_4$ is $L-R_{13}$. In one embodiment, $L-R_{13}$ is aminoalkyl. In one embodiment, the aminoalkyl is aminopropyl, alkylaminopropyl, or dialkylaminopropyl.

In one embodiment, $L-R_{13}$ is aminopropyl.

In one embodiment, $R_5$ is hydrogen, alkyl, aryl, or $COR_7$. In one embodiment, $R_5$ is $COR_7$.

In one embodiment, $R_7$ is substituted or unsubstituted aryl or heteroaryl. In one embodiment, $R_7$ is alkyl- or halogen-substituted aryl. In one embodiment, $R_7$ is substituted or unsubstituted phenyl, pyridyl, or pyrazinyl.

In one embodiment, $R_6$ is hydrogen, alkyl, chloro, or bromo.

In another embodiment, the heteroaryl-fused pyrimidinyl compounds have the formula (II):

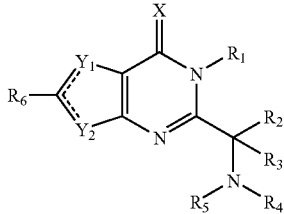

(II)

wherein X is O or S;

$Y_1$ is S, O, or $NR_{14}$ and $Y_2$ is $CR_{15}$; or $Y_1$ is $CR_{15}$ and $Y_2$ is S, O, or $NR_{14}$; or $Y_1$ is N and $Y_2$ is S, O, or $NR_{14}$; or $Y_1$ is S, O, $NR_{14}$ and $Y_2$ is N;

wherein, the dashed line represents a double bond to $Y_1$, when $Y_1$ is $CR_{15}$ or N, and a double bond to $Y_2$, when $Y_2$ is $CR_{15}$ or N;

$R_1$ is hydrogen, or substituted or unsubstituted alkyl, alkenyl, alkynyl, aryl, heteroaryl, heterocyclyl, alkylsulfonyl, or arylsulfonyl;

$R_2$ is hydrogen, or substituted or unsubstituted alkyl, alkenyl, aLkynyl, aryl, heteroaryl, heterocyclyl, alkylsulfonyl, arylsulfonyl, alkylcarboxy, aminocarboxy, aminocarbonyl, or alkylsulfonamido; or $COR_7$, $CO_2R_7$, $CONR_8R_9$, $S(O)_mR_{10}$, or $SO_2NR_{11}R_{12}$;

$R_3$ is cyano, substituted or unsubstituted arylsulfonyl, or $CONR_8R_9$;

$R_4$ is hydrogen, or substituted or unsubstituted alkyl, alkenyl, alkynyl, aryl, heteroaryl, or heterocyclyl; or $L-R_{13}$, wherein L is a C1-C10 saturated or unsaturated branched or unbranched carbon chain comprising one or more methylene groups, wherein one or more methylene groups are optionally independently replaced by O, N, or S; and wherein L is optionally substituted with one or two oxo groups and one or more C1-C10 branched or unbranched alkyl optionally substituted by one or more halogen atoms;

$R_5$ is hydrogen, or substituted or unsubstituted alkyl, alkenyl, alkynyl, aryl, alkoxy, aryl, heteroaryl, or heterocyclyl; or $COR_7$, $CO_2R_7$, $CONR_8R_9$, or $SO_{(m)}R_{10}$;

$R_6$ is hydrogen, halogen, hydroxy, nitro, amino, cyano, alkoxy, alkylthio, methylenedioxy, or haloalkoxy; or substituted or unsubstituted alkyl, alkenyl, alkynyl, aryl, heteroaryl, alkylamino, dialkylamino, alkylsulfonyl, arylsulfonyl, alkylcarboxy, carboxyamino, carboxyamido, aminocarboxy, aminocarbonyl, or alkylsulfonamido;

$R_7$, $R_8$, $R_9$, $R_{10}$, $R_{11}$, and $R_{12}$ are independently selected from hydrogen, or substituted or unsubstituted alkyl, alkenyl, alkynyl, aryl, heteroaryl, or heterocyclyl; or $R_8$ and $R_9$, or $R_{11}$ and $R_{12}$ taken together form a 3- to 7-membered carbocyclic or heterocyclic ring;

$R_{13}$ is amino, alkylamino, or dialkylamino; or substituted or unsubstituted guanidino or heterocyclyl;

$R_{14}$ and $R_{15}$ are independently selected from hydrogen, or substituted or unsubstituted alkyl, alkenyl, alkynyl, aryl, heteroaryl, or heterocyclyl;

m=0, 1, or 2; or the tautomers, pharmaceutically acceptable salts, or prodrugs thereof.

Suitable substituted alkyl groups include arylalkyl, heteroarylalkyl, heterocyclyalkyl, aminoalkyl, alkylaminoalkyl, dialkyaminoalkyl, and sulfonamidoalkyl groups.

In one embodiment, X is O.

In one embodiment, $R_1$ is arylalkyl. In one embodiment, the arylalkyl is benzyl.

In one embodiment, $R_2$ is hydrogen and $R_3$ is $CONR_8R_9$. In one embodiment, $R_8$ and $R_9$ are independently selected from hydrogen, methyl, ethyl, or isopropyl.

In one embodiment, $R_4$ is $L-R_{13}$. In one embodiment, $L-R_{13}$ is aminoalkyl. In one embodiment, the aminoalkyl is aminopropyl, alkylaminopropyl, or dialkylaminopropyl. In one embodiment, $L-R_{13}$ is aminopropyl.

In one embodiment, $R_5$ is hydrogen, alkyl, aryl, or $COR_7$. In one embodiment, $R_5$ is $COR_7$.

In one embodiment, $R_7$ is substituted or unsubstituted aryl or heteroaryl. In one embodiment, $R_7$ is alkyl- or halogen-substituted aryl. In one embodiment, $R_7$ is substituted or unsubstituted phenyl, pyridyl, or pyrazinyl.

In one embodiment, $R_6$ is hydrogen, alkyl, chloro, or bromo.

In another embodiment, the heteroaryl-fused pyrimidinyl compounds have the formula (III):

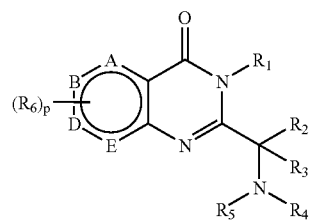

(III)

wherein, A, B, D, and E are independently selected from N, CH, or $CR_6$, with the proviso that at least one, but no more than two of A, B, D, or E are N;

$R_1$ is hydrogen, or substituted or unsubstituted alkyl, alkenyl, alkynyl, aryl, heteroaryl, heterocyclyl, alkylsulfonyl, or arylsulfonyl;

$R_2$ is hydrogen, or substituted or unsubstituted alkyl, alkenyl, alkynyl, aryl, heteroaryl, heterocyclyl, alkylsulfonyl, arylsulfonyl, alkylcarboxy, aminocarboxy, aminocarbonyl, or alkylsulfonamido; or $COR_7$, $CO_2R_7$, $CONR_8R_9$, $S(O)_mR_{10}$, or $SO_2NR_{11}R_{12}$;

$R_3$ is cyano, substituted or unsubstituted arylsulfonyl, or $CONR_8R_9$;

$R_4$ is hydrogen, or substituted or unsubstituted alkyl, alkenyl, alkynyl, aryl, heteroaryl, or heterocyclyl; or $L-R_{13}$, wherein L is a C1-C10 saturated or unsaturated branched or unbranched carbon chain comprising one or more methylene groups, wherein one or more methylene groups are optionally independently replaced by O, N, or S; and wherein L is optionally substituted with one or two oxo groups and one or more C1-C10 branched or unbranched alkyl optionally substituted by one or more halogen atoms;

$R_5$ is hydrogen, or substituted or unsubstituted alkyl, alkenyl, alkynyl, alkoxy, aryl, heteroaryl, or heterocyclyl; or $COR_7$, $CO_2R_7$, $CONR_8R_9$, or $SO_{(m)}R_{10}$;

$R_6$ is hydrogen, halogen, hydroxy, nitro, amino, cyano, alkoxy, alkylthio, methylenedioxy, or haloalkoxy; or substituted or unsubstituted alkyl, alkenyl, alkynyl, aryl, heteroaryl, alkylamino, dialkylamino, alkylsulfonyl, arylsulfonyl, alkylcarboxy, carboxyamino, carboxyamido, aminocarboxy, aminocarbonyl, or alkylsulfonamido;

$R_7$, $R_8$, $R_9$, $R_{10}$, $R_{11}$, and $R_{12}$ are independently selected from hydrogen, or substituted or unsubstituted alkyl, alkenyl, alkynyl, aryl, heteroaryl, or heterocyclyl; or $R_8$ and $R_9$, or $R_{11}$ and $R_{12}$ taken together form a 3- to 7-membered carbocyclic or heterocyclic ring;

$R_{13}$ is amino, alkylamino, or dialkylamino; or substituted or unsubstituted guanidino or heterocyclyl;

m=0, 1, or 2; and p=0, 1, 2, or 3; or the tautomers, pharmaceutically acceptable salts, or prodrugs thereof.

In one embodiment, A is N. In one embodiment when A is N, D is $CR_6$ and $R_6$ is chloro. In one embodiment when A is N, B and E are CH, D is $CR_6$, and $R_6$ is chloro.

Suitable substituted alkyl groups include arylalkyl, heteroarylalkyl, heterocyclylalkyl, aminoalkyl, alkylaminoalkyl, dialkyaminoalkyl, and sulfonamidoalkyl groups.

In one embodiment, X is O.

In one embodiment, $R_1$ is arylalkyl. In one embodiment, the arylalkyl is benzyl.

In one embodiment, $R_2$ is hydrogen and $R_3$ is $CONR_8R_9$. In one embodiment, $R_8$ and $R_9$ are independently selected from hydrogen, methyl, ethyl, or isopropyl.

In one embodiment, $R_4$ is $L-R_{13}$. In one embodiment, $L-R_{13}$ is aminoalkyl. In one embodiment, the aminoalkyl is aminopropyl, alkylaminopropyl, or dialkylaminopropyl. In one embodiment, $L-R_{13}$ is aminopropyl.

In one embodiment, $R_5$ is hydrogen, alkyl, aryl, or $COR_7$. In one embodiment, $R_5$ is $COR_7$.

In one embodiment, $R_7$ is substituted or unsubstituted aryl or heteroaryl. In one embodiment, $R_7$ is alkyl- or halogen-substituted aryl. In one embodiment, $R_7$ is substituted or unsubstituted phenyl, pyridyl, or pyrazinyl.

In one embodiment, $R_6$ is hydrogen, alkyl, chloro, or bromo.

In other aspects, the present invention provides methods for manufacture of compounds of formula (I), (II), and (III). Methods of making representative compounds are described in Example 1 and illustrated schematically below. It is further contemplated that, in addition to the compounds of formula (I), (II), and (III), intermediates and their corresponding methods of syntheses are included within the scope of the invention.

Compounds of formula (I) and (II) may be prepared as illustrated schematically in Schemes 1, 2, and 3 shown below.

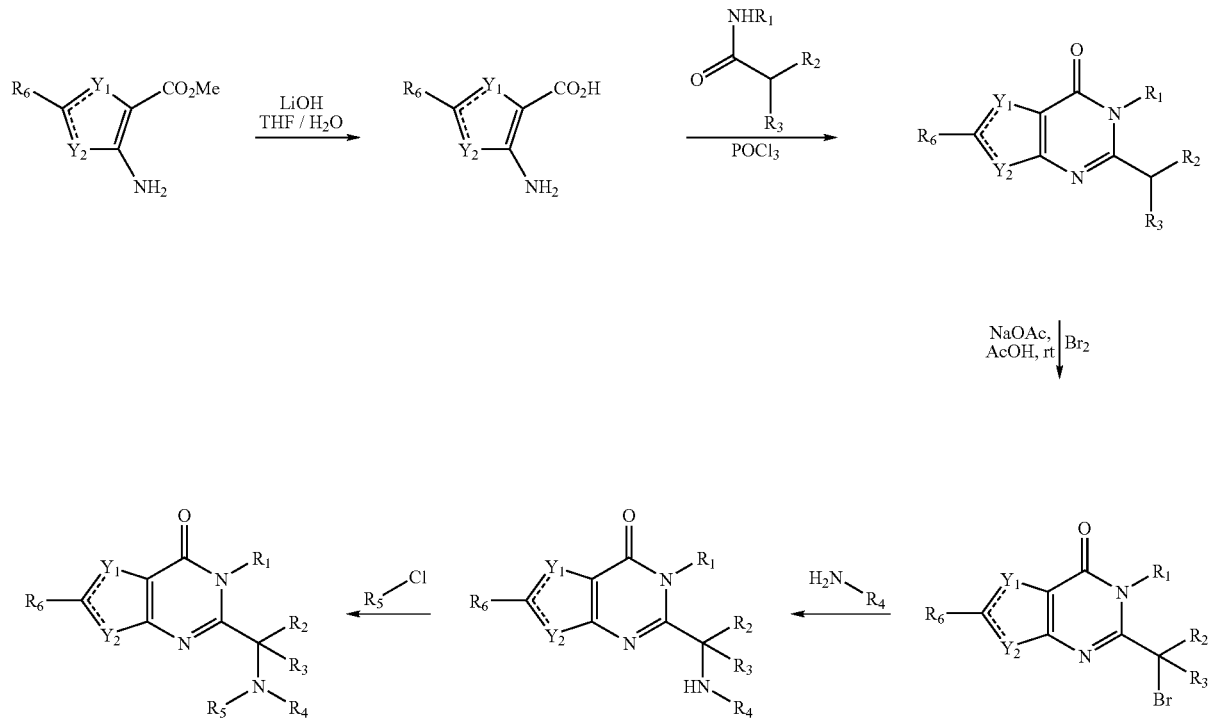

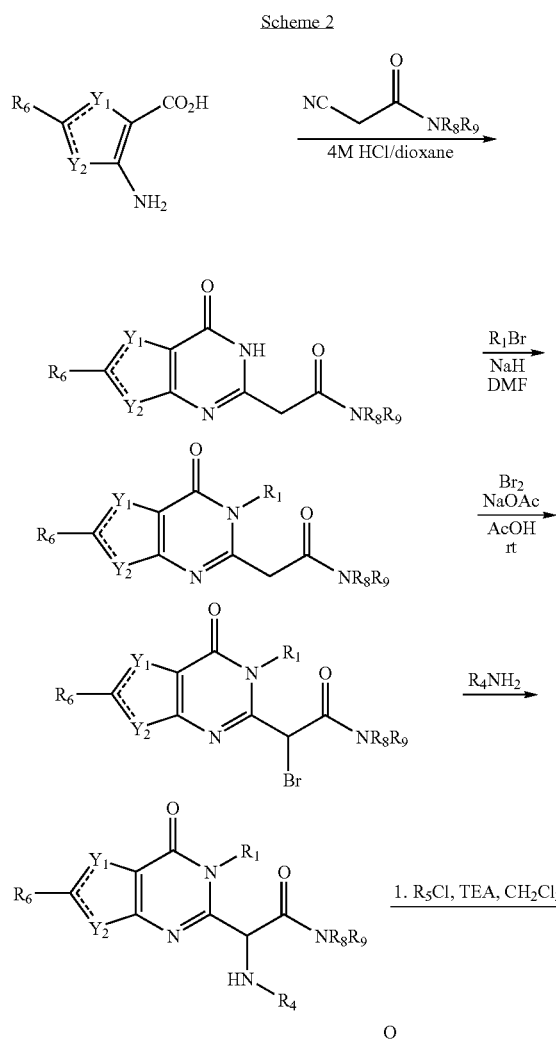
The synthesis of a representative thienyl-fused pyrimidin-4-one compound is described in Example 1. A schematic illustration of the preparation of the representative thienyl-fused pyrimidin-4-one compound described in Example 1 is shown below (Scheme 3).
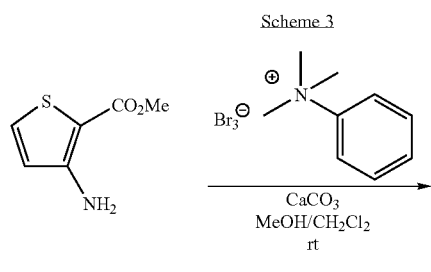
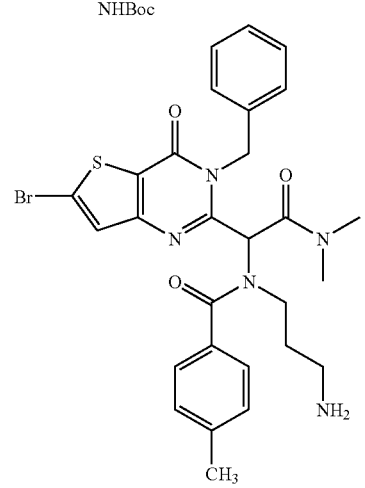

Representative thienyl-fused pyrimidin-4-one compounds of the invention are shown in Table 1.
Compounds of formula (I) and (III) may be prepared as illustrated schematically in Schemes 4 and 5 below.
Scheme 4
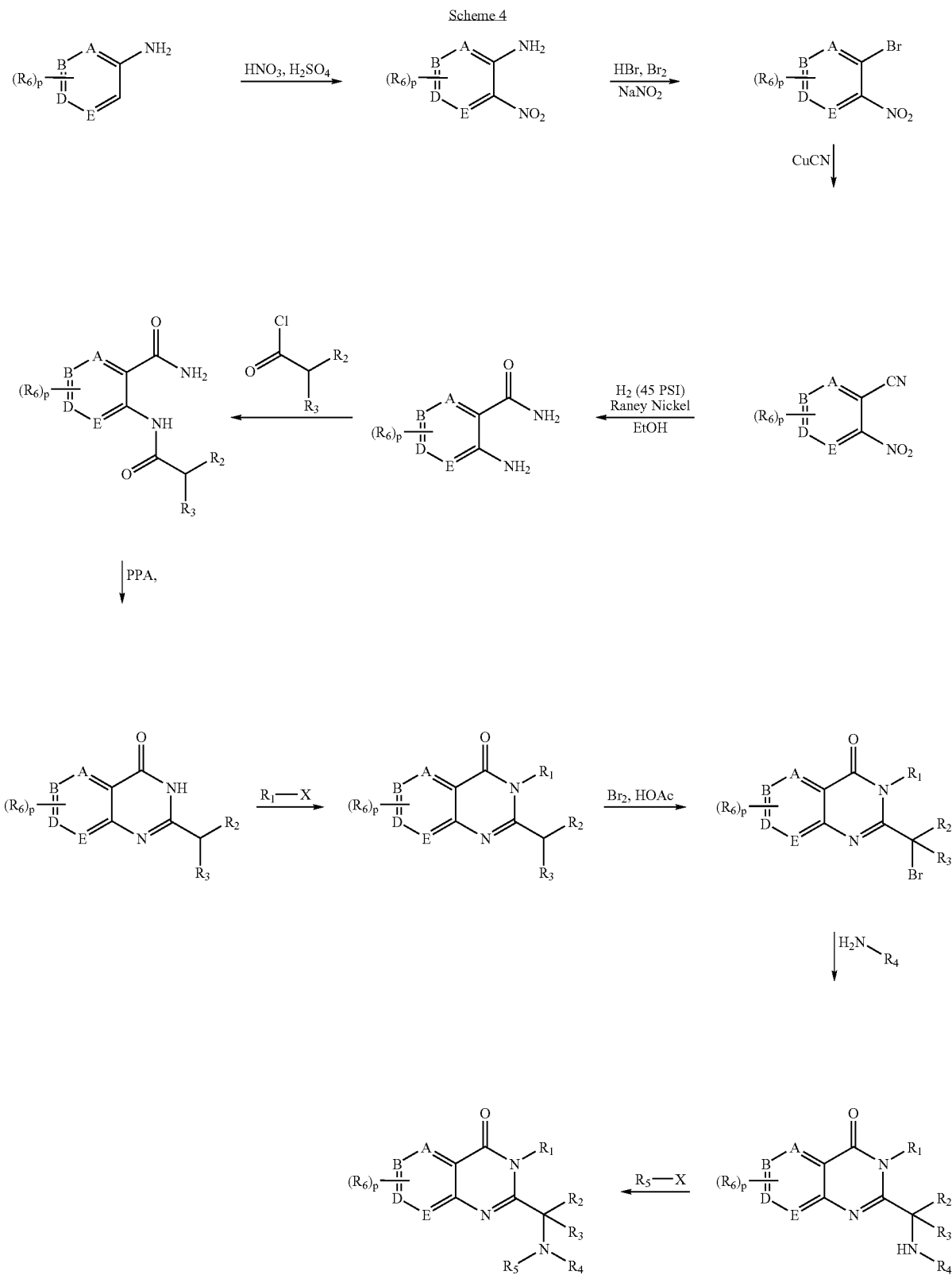

Scheme 5

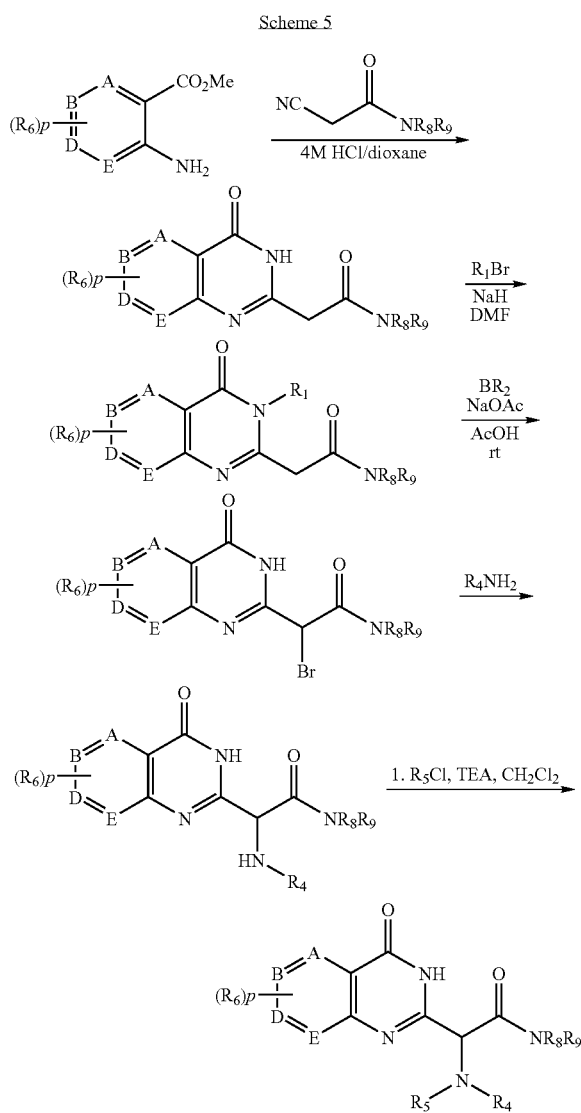

In other aspects, the present invention provides compositions that include at least one of the KSP inhibitors described herein, and methods that utilize the KSP inhibitors described herein.

In one aspect, the present invention provides pharmaceutical compositions comprising at least one heteroaryl-fused pyrimidinyl compound (e.g., a compound of formula (I), (II), or (III)) together with a pharmaceutically acceptable carrier suitable for administration to a human or animal subject, either alone or together with other anticancer agents.

A number of suitable anticancer agents to be used as combination therapeutics are contemplated for use in the compositions and methods of the present invention. Suitable anticancer agents to be used in combination with the compounds of the invention include agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g., IFN-a] and interleukins [e.g., IL-2]); adoptive immunotherapy agents; hematopoietic growth factors; agents that induce tumor cell differentiation (e.g., all-trans-retinoic acid); gene therapy reagents; antisense therapy reagents and nucleotides; tumor vaccines; inhibitors of angiogenesis, and the like. Numerous other examples of chemotherapeutic compounds and anti-cancer therapies suitable for coadministration with the compounds of formula (I), (II), or (III) are known to those skilled in the art.

In certain embodiments, anticancer agents to be used in combination with the compounds of the invention comprise agents that induce or stimulate apoptosis. Agents that induce apoptosis include, but are not limited to, radiation; kinase inhibitors (e.g., Epidermal Growth Factor Receptor [EGFR] kinase inhibitor, Vascular Growth Factor Receptor [VGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571, GLEEVEC® (imatinib mesylate), and Glivec);" antisense molecules; antibodies (e.g., herceptin and rituxan); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); and cancer chemotherapeutic drugs (e.g., irinotecan [camptosar], CPT-11, fludarabine [fludara], dacarbazine (DTIC), dexamethasone, mitoxantrone, mylotarg, VP-16, cisplatinum, 5-FU, doxrubicin, taxotere and taxol); cellular signaling molecules; ceramides and cytokines; and staurosprine; and the like.

In other aspects, the invention provides methods for using the compounds described herein. For example, the compounds described herein can be used in the treatment of cancer. The compounds described herein can also be used in the manufacture of a medicament for the treatment of cancer.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a heteroaryl-fused pyrimindinyl compound (e.g., a compound of formula (I), (II), or (III)), either alone or in combination with other anticancer agents.

In another embodiment, the present invention provides methods for treating a cellular proliferative disease in a human or animal subject in need of such treatment comprising, administering to said subject an amount of a heteroaryl-fused pyrimindinyl compound (e.g., a compound of formula (I), (II), or (III)) effective to reduce or prevent cellular proliferation or tumor growth in the subject.

In another embodiment, the present invention provides methods for treating a cellular proliferative disease in a human or animal subject in need of such treatment comprising administering to said subject an amount of a heteroaryl-fused pyrimindinyl compound (e.g., a compound of formula (I), (II), or (III)) effective to reduce or prevent cellular proliferation in the subject in combination with at least one additional agent for the treatment of cancer.

The present invention provides compounds that are inhibitors of KSP. The inhibitors are useful in pharmaceutical compositions for human or veterinary use where inhibition of KSP is indicated, for example, in the treatment of cellular proliferative diseases such as tumor and/or cancerous cell growth mediated by KSP. In particular, the compounds are useful in the treatment of human or animal (e.g., murine) cancers, including, for example, lung and bronchus;

prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

In another embodiment, the invention provides methods of treating an KSP mediated disorder. In one method, an effective amount of a heteroaryl-fused pyrimidinyl compound (e.g., a compound of formula (I), (II), or (III)) compound is administered to a patient (e.g., a human or animal subject) in need thereof to mediate (or modulate) KSP activity.

A representative assay for determining KSP inhibitory activity is described in Example 2.

The following definitions are provided to better understand the invention.

As used herein, the term "heteroaryl-fused pyrimidinyl compound" refers to a pyrimidinyl compound having a pyrimidinyl group fused to a heteroaryl group at positions 5 and 6 of the pyrimidinyl group.

The term "heteroaryl-fused pyrimidin-4-one compound" refers to a pyrimidinone compound having a carbonyl group at position 4 and that is fused to a heteroaryl group at positions 5 and 6.

"Alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase "alkyl groups" includes primary alkyl groups, secondary alkyl groups, and tertiary alkyl groups. Preferred alkyl groups include straight and branched chain alkyl groups and cyclic alkyl groups having 1 to 12 carbon atoms.

"Alkylene" refers to the same residues as noted above for "alkyl", but having two points of attachment. Exemplary alkylene groups include ethylene (—CH$_2$CH$_2$—), propylene (—CH$_2$CH$_2$CH$_2$—), dimethylpropylene (—CH$_2$C(CH$_3$)$_2$CH$_2$—), and cyclohexylpropylene (—CH$_2$CH$_2$CH(C$_6$H$_{13}$)—).

"Alkenyl" refers to straight chain, branched, or cyclic radicals having one or more carbon-carbon double bonds and from 2 to about 20 carbon atoms. Preferred alkenyl groups include straight chain and branched alkenyl groups and cyclic alkenyl groups having 2 to 12 carbon atoms.

"Alkynyl" refers to straight chain, branched, or cyclic radicals having one or more carbon-carbon triple bonds and from 2 to about 20 carbon atoms. Preferred alkynyl groups include straight chain and branched alkynyl groups having 2 to 12 carbon atoms.

Alkyl, alkenyl, and alkynyl groups may be substituted, such as with halo, hydroxy, amino, nitro and/or cyano groups, and the like. Representative of halo-substituted and hydroxy-substituted alkyl include chloromethyl, trichloromethyl, chloroethyl, hydroxyethyl, and the like. Other suitable substituted alkyl moieties include, for example, aralkyl, aminoalkyl, aminoaralkyl, carbonylaminoalkyl, alkylcarbonylaminoalkyl, arylcarbonylaminoalkyl, aralkylcarbonylaminoalkyl, aminoalkoxyalkyl and arylaminoalkyl.

"Alkoxy" refers to RO— wherein R is alkyl. Representative examples of alkoxy groups include methoxy, ethoxy, t-butoxy, trifluoromethoxy, and the like.

"Halogen" or "halo" refers to chloro, bromo, fluoro, and iodo groups. The term "haloalkyl" refers to an alkyl radical substituted with one or more halogen atoms. The term "haloalkoxy" refers to an alkoxy radical substituted with one or more halogen atoms.

"Amino" refers herein to the group —NH$_2$. The term "alkylamino" refers herein to the group —NRR' where R is alkyl and R' is hydrogen or alkyl. The term "arylamino" refers herein to the group —NRR' where R is aryl and R' is hydrogen, alkyl, or aryl. The term "aralkylamino" refers herein to the group —NRR' where R is aralkyl and R' is hydrogen, alkyl, aryl, or aralkyl.

"Alkoxyalkyl" refers to the group -alk$_1$—O-alk$_2$ where alk$_1$ is alkyl or alkenyl, and alk$_2$ is alkyl or alkenyl. The term "aryloxyalkyl" refers to the group -alkyl O-aryl. The term "aralkoxyalkyl" refers to the group -alkylenyl-O-aralkyl.

"Alkoxyalkylamino" refers herein to the group —NR—(alkoxyalkyl), where R is typically hydrogen, aralkyl, or alkyl.

"Aminocarbonyl" refers herein to the group —C(O)—NH$_2$. "Substituted aminocarbonyl" refers herein to the group —C(O)—NRR' where R is alkyl and R' is hydrogen or alkyl. The term "arylaminocarbonyl" refers herein to the group —C(O)—NRR' where R is aryl and R' is hydrogen, alkyl or aryl. "Aralkylaminocarbonyl" refers herein to the group —C(O)—NRR' where R is aralkyl and R' is hydrogen, alkyl, aryl, or aralkyl.

"Aminosulfonyl" refers herein to the group —S(O)$_2$—NH$_2$. "Substituted aminosulfonyl" refers herein to the group —S(O)$_2$—NRR' where R is alkyl and R' is hydrogen or alkyl. The term "aralkylaminosulfonlyaryl" refers herein to the group -aryl-S(O)$_2$—NH-aralkyl.

"Carbonyl" refers to the divalent group —C(O)—.

"Carbonyloxy" refers generally to the group —C(O)—O. Such groups include esters, —C(O)—O—R, where R is alkyl, cycloalkyl, aryl, or aralkyl. The term "carbonyloxycycloalkyl" refers generally herein to both a "carbonyloxycarbocycloalkyl" and a "carbonyloxyheterocycloalkyl", i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl.

"Sulfonyl" refers herein to the group —SO$_2$—. "Alkylsulfonyl" refers to a substituted sulfonyl of the structure —SO$_2$R— in which R is alkyl. Alkylsulfonyl groups employed in compounds of the present invention are typically alkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —SO$_2$-aryl. The term "aralkylsulfonyl"

refers herein to the group —SO$_2$-aralkyl. The term "sulfonamido" refers herein to —SO$_2$NH$_2$.

"Carbonylamino" refers to the divalent group —NH—C(O)— in which the hydrogen atom of the amide nitrogen of the carbonylamino group can be replaced alkyl, aryl, or aralkyl group. Such groups include moieties such as carbamate esters (—NH—C(O)—O—R) and amides —NH—C(O)—R, where R is a straight or branched chain alkyl, cycloalkyl, or aryl or aralkyl. The term "alkylcarbonylamino" refers to alkylcarbonylamino where R is alkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is aralkyl.

"Guanidino" or "guanidyl" refers to moieties derived from guanidine, H$_2$N—C(=NH)—NH$_2$. Such moieties include those bonded at the nitrogen atom carrying the formal double bond (the "2"-position of the guanidine, e.g., diaminomethyleneamino, (H$_2$N)$_2$C=NH—)) and those bonded at either of the nitrogen atoms carrying a formal single bond (the "1-" and/or "3"-positions of the guandine, e.g., H$_2$N—C(=NH)—NH—)). The hydrogen atoms at any of the nitrogens can be replaced with a suitable substituent, such as alkyl, aryl, or aralkyl.

"Amidino" refers to the moieties R—C(=N)—NR'— (the radical being at the "N$^1$" nitrogen) and R(NR')C=N— (the radical being at the "N$^2$" nitrogen), where R and R' can be hydrogen, alkyl, aryl, or aralkyl.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Substituted heterocycle," "heterocyclic group," "heterocycle," or "heterocyclyl," as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. The term "heterocycle" thus includes rings in which nitrogen is the heteroatom as well as partially and fully-saturated rings. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclic moieties can be unsubstituted or monosubstituted or disubstituted with various substituents independently selected from hydroxy, halo, oxo (C=O), alkylimino (RN=, wherein R is alkyl or alkoxy group), amino, alkylamino, dialkylamino, acylaminoalkyl, alkoxy, thioalkoxy, polyalkoxy, alkyl, cycloalkyl or haloalkyl.

The heterocyclic groups may be attached at various positions as will be apparent to those having skill in the organic and medicinal chemistry arts in conjunction with the disclosure herein.

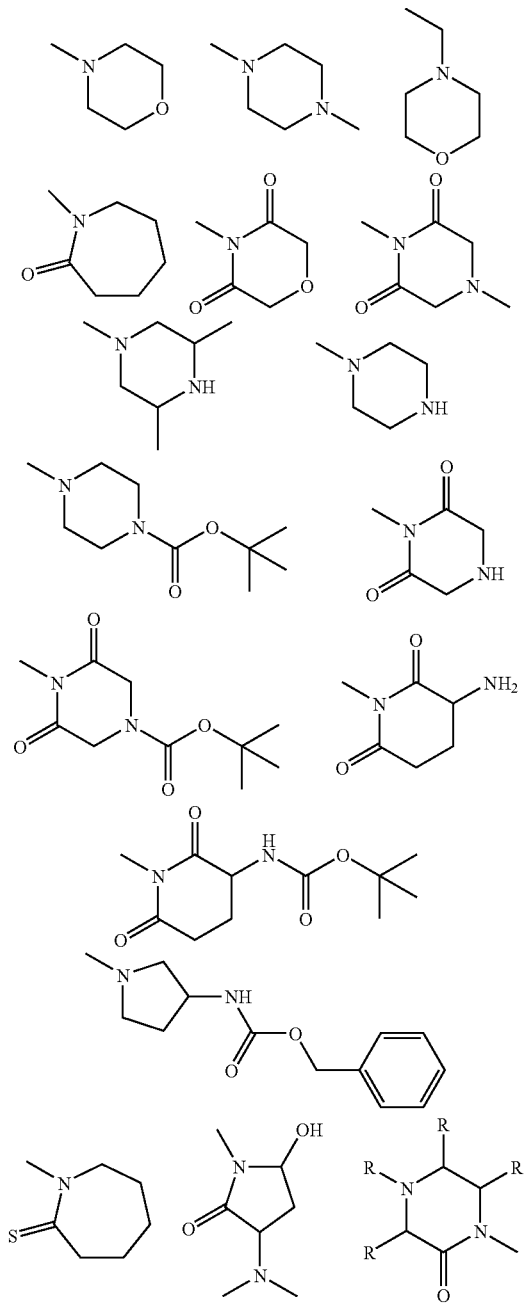

where R is H or a heterocyclic substituent, as described herein.

Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e.,

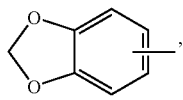

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" or "arylalkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein.

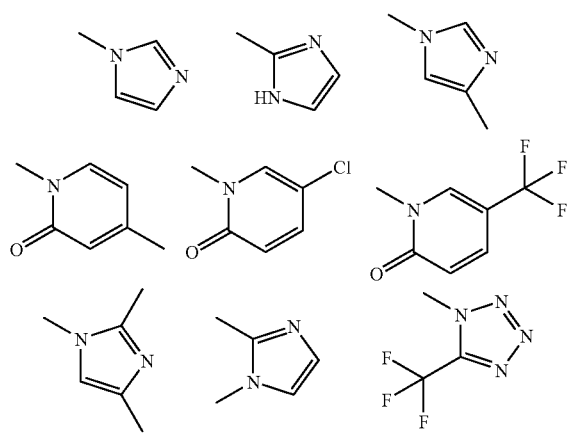

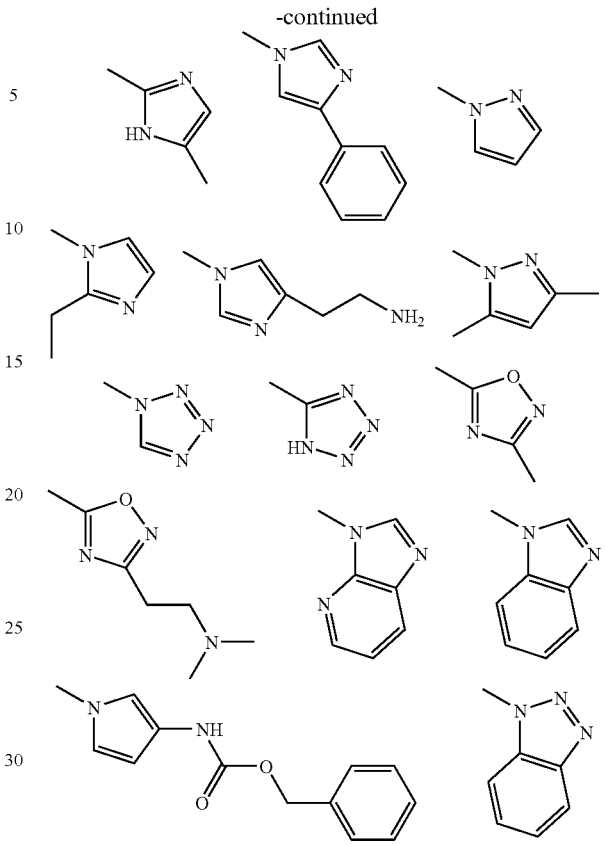

Representative heteroaryl's include, for example, imidazolyl, pyridyl, thiazolyl, triazolyl benzimidazolyl, benzothiazolyl, and benzoxazolyl.

"Biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)phenyl]acetamide, 1,4-diphenylbenzene, N-[4-(2-phenylethynyl)phenyl]-2-[benzylamino]acetamide, 2-amino-N-[4-(2-phenylethynyl)phenyl]propanamide, 2-amino-N-[4-(2-phenylethynyl)phenyl]acetamide, 2-(cyclopropylamino)-N-[4-(2-phenylethynyl)phenyl]acetamide, 2-(ethylamino)-N-[4-(2-phenylethynyl)phenyl]acetamide, 2-[(2-methylpropyl)amino]-N-[4-(2-phenylethynyl)phenyl]acetamide, 5-phenyl-2H-benzo[d]1,3-dioxolene, 2-chloro-1-methoxy-4-phenylbenzene, 2-[(imidazolylmethyl)amino]-N-[4-(2-phenylethynyl)phenyl]acetamide, 4-phenyl-1-phenoxybenzene, N-(2-aminoethyl)[4-(2-phenylethynyl)phenyl]carboxamide, 2-{[(4-fluorophenyl)methyl]-amino}-N-[4-(2-phenylethynyl)phenyl]acetamide, 2-{[(4-methylphenyl)methyl]amino}-N-[4-(2-phenylethynyl)phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethylmethylamino)-N-[4-(2-phenylethynyl)phenyl]acetamide, 2-(butylamino)-N-[4-(2-phenylethynyl)phenyl]acetamide, N-[4-(2-phenylethynyl)phenyl]-2-(4-pyridylamino)acetamide, N-[4-(2-phenylethynyl)phenyl]-2-

(quinuclidin-3-ylamino)acetamide, N-[4-(2-phenylethynyl) phenyl]pyrrolidin-2-ylcarboxamide, 2-amino-3-methyl-N-[4-(2-phenylethynyl)phenyl]butanamide, 4-(4-phenylbuta-1,3-diynyl)phenylamine, 2-(dimethylamino)-N-[4-(4-phenylbuta-1,3-diynyl)phenyl]acetamide, 2-(ethylamino)-N-[4-(4-phenylbuta-1,3-diynyl)phenyl]acetamide, 4-ethyl-1-phenylbenzene, 1-[4-(2-phenylethynyl)phenyl]ethan-1-one, N-(1-carbamoyl-2-hydroxypropyl)[4-(4-phenylbuta-1,3-diynyl)phenyl]carboxamide, N-[4-(2-phenylethynyl) phenyl]propanamide, 4-methoxyphenyl phenyl ketone, phenyl-N-benzamide, (tert-butoxy)-N-[(4-phenylphenyl) methyl]carboxamide, 2-(3-phenylphenoxy)ethanehydroxamic acid, 3-phenylphenyl propanoate, 1-(4-ethoxyphenyl)-4-methoxybenzene, and [4-(2-phenylethynyl)phenyl] pyrrole.

"Heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2phenylethynyl)pyrazine, 2-phenylthiophene, phenylimidazole, 3-(2-piperazinylphenyl)furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenylpyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl (2-thienyl))-methane, 5-[(4-methylpiperazinyl)methyl]-2-phenylthiophene, 2-(4-ethylphenyl)thiophene, 4-methylthio-1-(2-thienyl)benzene, 2-(3-nitrophenyl) thiophene, (tert-butoxy)-N-[(5-phenyl(3-pyridyl))methyl] carboxamide, hydroxy-N-[(5-phenyl(3-pyridyl))methyl]-amide, 2-(phenylmethylthio)pyridine, and benzylimidazole.

"Heteroarylheteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl(3-pyrazin-2-yl(4-pyridyl))amine, and dimethyl {2-[2-(5-methylpyrazin-2-yl) ethynyl](4-pyridyl)}amine.

"Optionally substituted" or "substituted" refers to the replacement of hydrogen with a monovalent or divalent radical. Suitable substitution groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, alkyl, haloalkyl, alkyamino, haloalkylamino, alkoxy, haloalkoxy, alkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like.

The substitution group can itself be substituted. The group substituted onto the substitution group can be carboxyl, halo; nitro, amino, cyano, hydroxyl, alkyl, alkoxy, aminocarbonyl, —SR, thioamido, —SO$_3$H, —SO$_2$R or cycloalkyl, where R is typically hydrogen, hydroxyl or alkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

"Carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, alkyl esters, secondary amides and the like.

Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," *Pure Appl. Chem.* 45:13-30, 1976. The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the "Chemical Abstracts Index Guide," Appendix IV, paragraph 203, 1987.

As used herein, the term "pharmaceutically acceptable salts" refers to the nontoxic acid or alkaline earth metal salts of the compounds of formula (I), (II), or (III). These salts can be prepared in situ during the final isolation and purification of the compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), (II), or (III), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield a parent compound of one of formula (I), (II), or (III), for example, by hydrolysis in blood. A thorough discussion of prodrugs is provided in Higuchi, T., and V. Stella, "Prodrugs as Novel Delivery Systems," *A.C.S. Symposium Series* 14, and in "Bioreversible Carriers in Drug Design," in Edward B. Roche (ed.), *American Pharmaceutical Association*, Pergamon Press, 1987, both of which are incorporated herein by reference.

The term "cancer" refers to cancer diseases that can be beneficially treated by the inhibition of KSP, including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

Effective amounts of the compounds of the invention generally include any amount sufficient to detectably inhibit KSP activity by any of the assays described herein, by other KSP activity assays known to those having ordinary skill in the art, or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, GLEEVEC® (imatinib mesylate), herceptin, 5-fluorouracil, leucovorin, carboplatin, cisplatin, taxanes, tezacitabine, cyclophosphamide, vinca alkaloids, imatinib, anthracyclines, rituximab, trastuzumab, topoisomerase I inhibitors, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan, et al, *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formula (I), (II), or (III) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-ABl tyrosine kinase. The afflicted patients are responsive to GLEEVEC® (imatinib mesylate), a small molecule tyrosine kinase inhibitor, as a result of inhibition of Abl kinase activity. However, many patients with advanced stage disease respond to GLEEVEC® (imatinib mesylate) initially, but then relapse later due to resistance-conferring mutations in the Abl kinase domain. In vitro studies have demonstrated that BCR-Avl employs the Raf kinase pathway to elicit its effects. In addition, inhibiting more than one kinase in the same pathway provides additional protection against resistance-conferring mutations. Accordingly, in another aspect of the invention, the compounds of formula (I), (II), or (III) are used in combination with at least one additional agent, such as GLEEVEC® (imatinib mesylate), in the treatment of hematological cancers, such as chronic myelogenous leukemia (CML), to reverse or prevent resistance to the at least one additional agent.

In another aspect of the invention, kits that include one or more compounds of the invention are provided. Representative kits include a compound of formula (I), (II), or (III) and a package insert or other labeling including directions for treating a cellular proliferative disease by administering an KSP inhibitory amount of the compound.

The present invention will be understood more readily by reference to the following examples, which are provided by way of illustration and are not intended to be limiting of the present invention.

EXAMPLES

Referring to the examples that follow, compounds of the present invention were synthesized using the methods described herein, or other methods, which are well known in the art. The compounds were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 rm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses are reported as those of the protonated parent ions.

GCMS analysis was performed on a Hewlett Packard instrument (HP6890 Series gas chromatograph with a Mass Selective Detector 5973; injector volume: 1 μL; initial column temperature: 50° C.; final column temperature: 250C; ramp time: 20 minutes; gas flow rate: 1 mL/min;

column: 5% phenyl methyl siloxane, Model No. HP 190915-443, dimensions: 30.0 m×25 m×0.25 m).

Nuclear magnetic resonance (NMR) analysis was performed with a Varian 300 Mhz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds was assessed by elemental analysis (Desert Analytics, Tucson, Ariz.)

Melting points were determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

The following are abbreviations used in the examples:

| | |
|---|---|
| AcOH: | Acetic acid |
| aq: | Aqueous |
| ATP: | Adenosine triphosphate |
| 9-BBN | 9-Borabicyclo[3.3.1]nonane |
| Boc: | tert-butoxycarbonyl |
| Celite | Filter agent |
| DAP or Dap: | Diaminopropionate |
| DCM: | Dichloromethane |
| DEAD: | Diethyl azodicarboxylate |
| DIEA: | Diisopropylethylamine |
| DMAP | 4-Dimethylaminopyridine |
| DME: | 1,2-Dimethoxyethane |
| DMF: | N,N-Dimethylformamide |
| DMSO: | Dimethyl sulfoxide |
| DPPA: | Diphenyl phosphoryl azide |
| Et$_3$N: | Triethylamine |
| EDC: | N-(3-Dimethylaminopropyl)-N'-ethylcarbodiimide |
| EDCI: | 1-(3-Dimethylaminopropyl)3-ethylcarbodiimide |
| EtOAc: | Ethyl acetate |
| EtOH: | Ethanol |
| Fmoc: | 9-Fluorenylmethoxycarbonyl |
| Gly-OH: | Glycine |
| HATU: | O-(7-Azabenzotriaazol-1-yl)-N,N,N'N'-tetramethyluronium hexafluorophosphate |
| HBTU: | 2-(1H-Benzotriazol-1-yl)-1,1,3,3-tetramethyluronium hexafluorophosphate |
| Hex: | Hexane |
| HOBt: | Butyl alcohol |
| HOBT: | 1-Hydroxybenzotriazole |
| HPLC: | High Pressure Liquid Chromatography |
| NIS | N-iodosuccinimide |
| IC$_{50}$ value: | The concentration of an inhibitor that causes a 50% reduction in a measured activity. |
| iPrOH: | Isopropanol |
| LC/MS: | Liquid Chromatography/Mass Spectrometry |
| LRMS: | Low Resolution Mass Spectrometry |
| MeOH: | Methanol |
| NaOMe: | Sodium methoxide |
| nm: | Nanometer |
| NMP: | N-Methylpyrrolidone |
| PPA | Polyphosphoric acid |
| PPh$_3$: | Triphenyl phosphine |
| PTFE | Polytetrafluoroethylene |
| RP-HPLC: | Reversed-phase high-pressure liquid chromatography |
| RT: | Room temperature |
| sat: | Saturated |
| TEA: | Triethylamine |

-continued

| | |
|---|---|
| TFA: | Trifluoroacetic acid |
| THF: | Tetrahydrofuran |
| Thr: | Threonine |
| TLC: | Thin Layer Chromatography |
| Trt-Br: | Tert-butyl bromide |

Nomenclature for the Example compounds was provided using ACD Name version 5.07 software (Nov. 14, 2001) available from Advanced Chemistry Development, Inc. Some of the compounds and starting materials were named using standard IUPAC nomenclature.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the above disclosure.

Example 1

N-(3-aminopropyl)-N-[1-(3-benzyl-6-bromo-4-oxo-3,4-dihydrothienor[3,2-d]pyrimidin-2-yl)-2-(dimethylamino)-2-oxoethyl]-4-methylbenzamide (Compound 5 in Table 1)

Step 1. Methyl 3-amino-5-bromothiophene-2-carboxylate

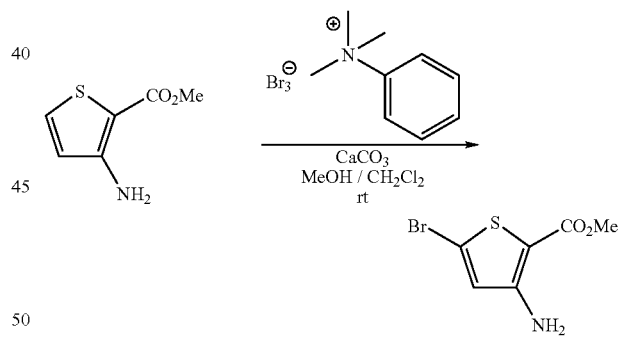

Methyl-3-amino-2-thiophene carboxylate (1 eq. 25 g) was dissolved in 250 ml methylene chloride and 250 ml of methanol. Phenyl trimethylammonium tribromide (3 eq. 180 g) was added followed by calcium carbonate (4 eq. 63.75 g) and the reaction was left stirring at room temperature overnight. The calcium carbonate was filtered off and the filtrate concentrated down and water (750 ml) was added followed by ethyl acetate (1 L). The ethyl acetate layer was washed with more water, sodium thiosulfate, saturated sodium bicarbonate and saturated sodium chloride. The organic layer was dried over magnesium sulfate, filtered and the filtrate was concentrated under reduced pressure. The crude product was purified by flash chromatography to yield 21.46 g (57%) of methyl 3-amino-5-bromothiophene-2-carboxylate as a light brown oil, MH$^+$=238.1.

Step 2. 2-(6-Bromo-4-oxo(3-hydrothiopheno[3,2-d]pyrimidin-2-yl))-N,N-dimethylacetamide

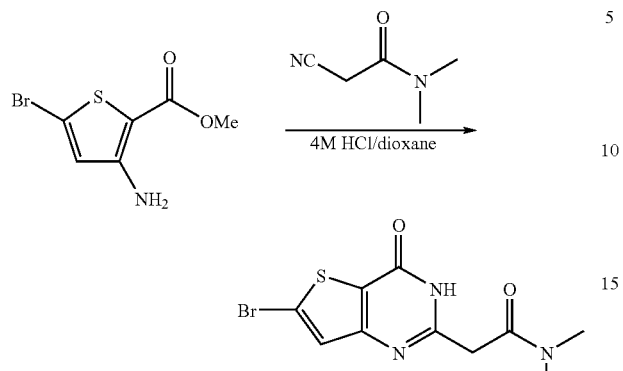

Methyl 3-amino-5-bromothiophene-2-carboxylate (1 eq. 21.4 g) and 2-Cyano-N,N-dimethyl-acetamide (1.2 eq. 12.2 g) were dissolved in 4M HCl/dioxane (0.7 M, 125 ml). The reaction was stirred at room temperature overnight. Then, the reaction mixture was heated to 80° C. overnight. The mixture was cooled to room temperature and the product precipitated out. It was collected over a Buchner funnel. The crude precipitate was sonicated with water (200 ml), filtered, and dried by vacuum on a Buchner funnel to yield 5.96 g (21%) of 2-(6-bromo-4-oxo(3-hydrothiopheno[3,2-d]pyrimidin-2-yl))-N,N-dimethylacetamide as a pink solid, $MH^+=318.0$.

Step 3. 2-[6-Bromo-4-oxo-3-benzyl(3-hydrothiopheno[3,2-d]pyrimidin-2-yl)]-N,N-dimethylacetamide

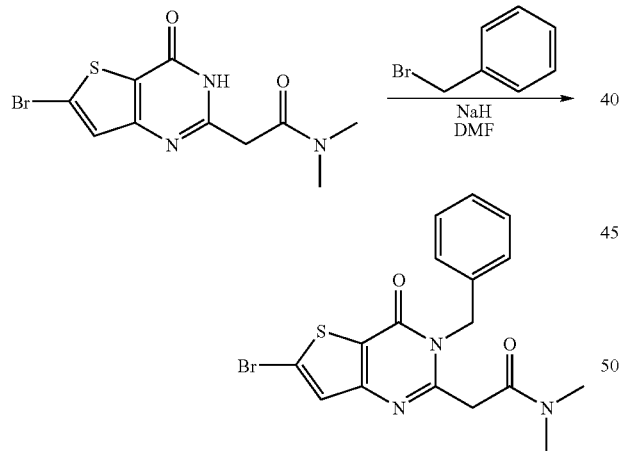

2-(6-bromo-4-oxo(3-hydrothiopheno[3,2-d]pyrimidin-2-yl))-N,N-dimethylacetamide (1 eq. 2 g) was dissolved in DMF (20 ml) and cooled to 0° C. Sodium hydride (1.5 eq. 227 mg) was added followed by benzyl bromide (1.5 eq. 1.13 ml). The reaction mixture was stirred at room temperature overnight. The mixture was cooled to 0° C. and quenched with saturated sodium bicarbonate (20 ml). Water was added (50 ml) followed by ethyl acetate. The layers were separated and the organic layer was further washed with saturated sodium bicarbonate, water and saturated sodium chloride. The organic layer was dried over sodium sulfate, decanted and concentrated. The crude mixture was purified by Flash chromatography to yield 1.57 g of the two isomers (N-benzylated and O-benzylated). The resulting solid was triturated with methanol to crash out most of the desired N-benzylated isomer. The remaining mixture was purified on PREP HPLC and free-based to yield in total 1.00 g (39%) of 2-[6-bromo-4-oxo-3-benzyl(3-hydrothiopheno[3,2-d]pyrimidin-2-yl)]-N,N-dimethylacetamide, $MH^+=408.0$.

Step 4. 2-Bromo-2-[6-bromo-4-oxo-3-benzyl(3-hydrothiopheno[3,2-d]pyrimidin-2-yl)]-N,N-dimethylacetamide

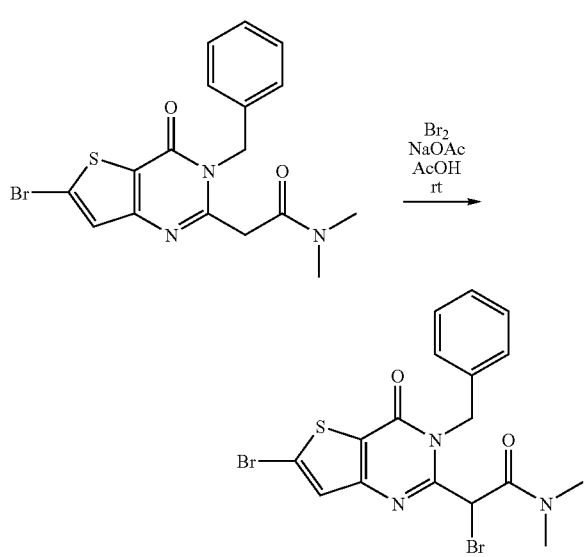

2-[6-bromo-4-oxo-3-benzyl(3-hydrothiopheno[3,2-d]pyrimidin-2-yl)]-N,N-dimethylacetamide (1 eq. 988 mg) was dissolved in 20 ml of acetic acid then sodium acetate (2 eq. 398 mg) was added followed by bromine (1 eq. 125 ul). After about 2 h 0.5 more equivalents of sodium acetate and 0.5 equivalent of bromine were added. The reaction was complete after 2 h more. Water was added to the reaction and the product was extracted into ethyl acetate then later washed with more water, saturated sodium bicarbonate and saturated sodium chloride. The organic layer was dried over sodium sulfate, decanted and concentrated to yield 1.06 g (90%) of 2-bromo-2-[6-bromo-4-oxo-3-benzyl(3-hydrothiopheno[3,2-d]pyrimidin-2-yl)]-N,N-dimethylacetamide, $MH^+=486.1$.

Step 5. 2-({3-[(tert-Butoxy)carbonylamino]propyl}amino)-2-[6-bromo-4-oxo-3-benzyl(3-hydrothiopheno[3,2-d]pyrimidin-2-yl)]-N,N-dimethylacetamide

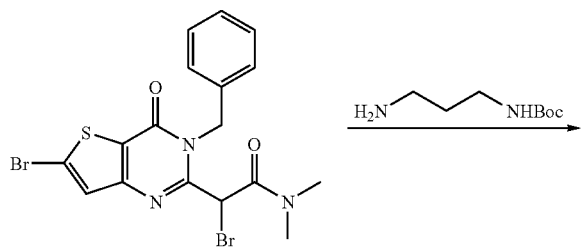

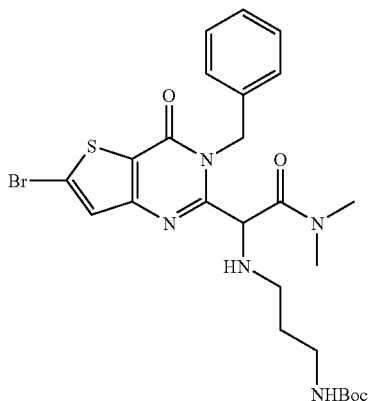

To a solution of N-bocpropylamine (3 eq. 1.14 g) in 15 ml of dimethyl formamide, was added 2-bromo-2-[6-bromo-4-oxo-3-benzyl(3-hydrothiopheno[3,2-d]pyrimidin-2-yl)]-N,N-dimethylacetamide (1 eq. 1.06 g). The reaction mixture was stirred at room temperature overnight. Ethyl acetate (500 ml) was added to the mixture and the organic layer was washed with saturated sodium bicarbonate, water (4 washes), and saturated sodium chloride. The organic layer was dried over sodium sulfate, decanted and concentrated down. The crude mixture was purified by flash chromatography to yield 428 mg (34%) of 2-({3-[(tert-butoxy)carbonylamino]propyl} amino)-2-[6-bromo-4-oxo-3-benzyl(3-hydrothiopheno[3,2-d]pyrimidin-2-yl)]-N,N-dimethylacetamide, $MH^+$=580.3.

Step 6. N-(3-Aminopropyl)-N-[1-(3-benzyl-6-bromo-4-oxo-3,4-dihydrothieno[3,2-d]pyrimidin-2-yl)-2-(dimethylamino)-2-oxoethyl]-4-methylbenzamide

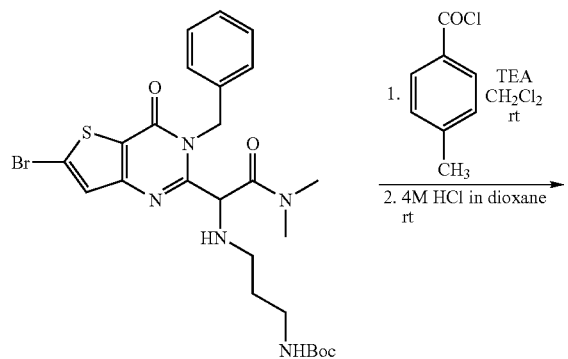

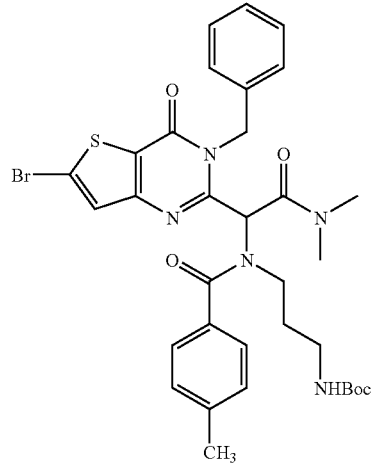

2-({3-[(tert-butoxy)carbonylamino]propyl}amino)-2-[6-bromo-4-oxo-3-benzyl(3-hydrothiopheno[3,2-d]pyrimidin-2-yl)]-N,N-dimethylacetamide (1 eq. 75 mg) was dissolved in 2 ml of methylene chloride and the solution was cooled to 0° C. Acid chloride (3 eq. 51 ul) was added followed by the addition of triethylamine (5 eq. 91 ul). The reaction mixture was allowed to warm to room temperature and to stir at room temperature overnight. 30 ml of methylene chloride was added to the mixture. The organic layer was washed with water, saturated bicarbonate, saturated sodium chloride, filtered and the filtrate was dried over sodium sulfate, decanted and concentrated in vacuo. The crude mixture was purified by flash chromatography to yield 57.5 mg (64%) of 2-(N-{3-[(tert-butoxy)carbonylamino]propyl}(4-methylphenyl)carbonylamino)-2-[6-bromo-4-oxo-3-benzyl(3-hydrothiopheno[3,2-d]pyrimidin-2-yl)]-N,N-dimethylacetamide, $MH^+$=696.1.

2-(N-{3-[(tert-butoxy)carbonylamino]propyl} (4-methylphenyl)carbonylamino)-2-[6-bromo-4-oxo-3-benzyl(3-hydrothiopheno[3,2-d]pyrimidin-2-yl)]-N,N-dimethylacetamide (1 eq. 53 mg) was dissolved in 4M HCl in dioxane (1 ml). The reaction mixture was stirred at room temperature for 3 h. 20 ml of ether was added and decanted off. This was repeated 2× and the reaction mixture was concentrated to yield a white solid. Precipitate in the ether washes was also filtered and combined with the solid. The combined solids yielded 25 mg (52%) of 2-[N-(3-aminopropyl)(4-methylphenyl)carbonylamino]-2-[6-bromo-4-oxo-3-benzyl(3-hydrothiopheno[3,2-d]pyrimidin-2-yl)]-N,N-dimethylacetamide as the HCl salt, $MH^+$=598.1.

Compound 5 in Table 1 was prepared as described above. Compounds 1-4 and 6 in Table 1 were made in analogous manner as described above for compound 5 starting from product of step 5 of Example 1: 1 2-({3-[(tert-butoxy)carbonylamino]propyl}amino)-2-[6-bromo-4-oxo-3-benzyl(3-hydrothiopheno[3,2-d]pyrimidin-2-yl)]-N,N-dimethylacetamide and corresponding aryl-C(=O)—Cl or heteroaryl-C(=O)-chloride.

TABLE 1

| Compound | Structure | MH+ | Name |
|---|---|---|---|
| 1 | 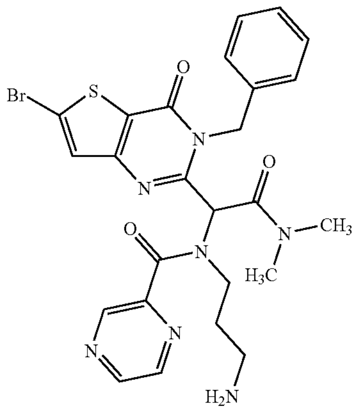 | 584.3 | N-(3-aminopropyl)-N-[1-(3-benzyl-6-bromo-4-oxo-3,4-dihydrothieno[3,2-d]pyrimidin-2-yl)-2-(dimethylamino)-2-oxoethyl]pyrazine-2-carboxamide |
| 2 | 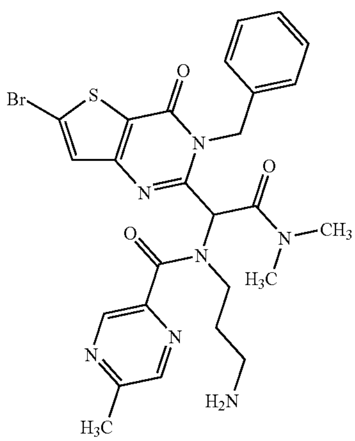 | 598.3 | N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-5-methylpyrazine-2-carboxamide |
| 3 | 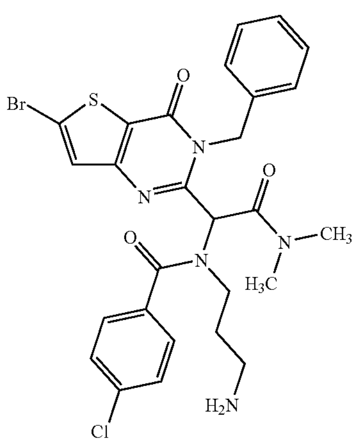 | 618.0 | N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-4-chlorobenzamide |

TABLE 1-continued

| Compound | Structure | MH+ | Name |
|---|---|---|---|
| 4 | 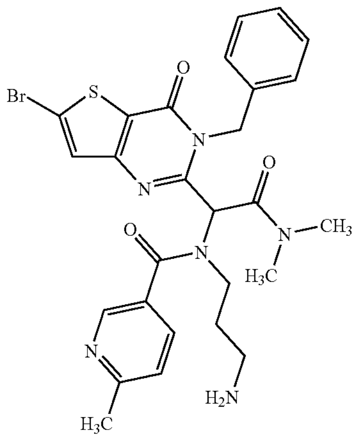 | 599.0 | N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-6-methylnicotinamide |
| 5 | 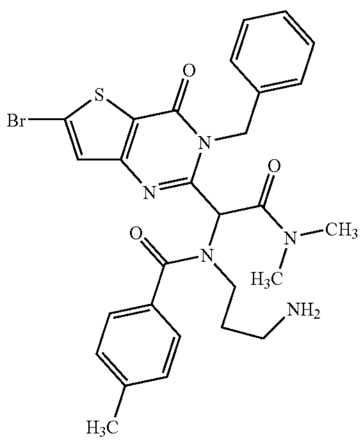 | 598.3 | N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-4-methylbenzamide |
| 6 | 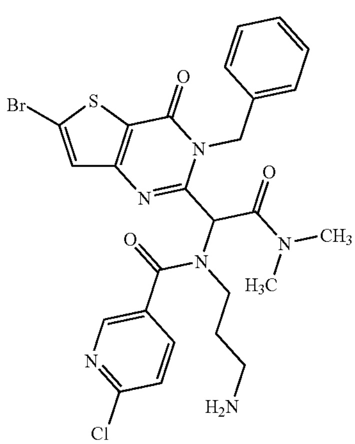 | 619.0 | N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-6-chloronicotinamide |

Using the procedure described in Example 2, compounds 1-6 were shown to have an Eg5 inhibitory activity at an $IC_{50}$ or less than about 25 μM. Some of the compounds have an $IC_{50}$ of less than about 10 μM, and certain others of the compounds have an $IC_{50}$ of less than 1 μM.

Example 2

Assay for Determining KSP Activity

In this example, a representative in vitro assay for determining KSP activity is described.

Purified microtubules from bovine brain were purchased from Cytoskeleton Inc. The motor domain of human KSP (KSP, KNSL1) was cloned and purified to a purity of greater than 95%. Biomol Green was purchased from Affinity Research Products Ltd.

Microtubules and the KSP motor protein were diluted in assay buffer (20 mM Tris-HCl, pH 7.5, 1 mM $MgCl_2$, 10 mM DTT and 0.25 mg/mL BSA) to a concentration of 35 ug/mL for microtubules and 45 nM for KSP. The microtubule/KSP mixture was then pre-incubated at 37° C. for 10 min to promote the binding of KSP to microtubules. ATP was also diluted to a concentration of 300 uM in the same assay buffer. To each well of the testing plate (384 well plate) containing 1.25 uL of compounds in DMSO or DMSO only, 25 uL of ATP solution. To start the reaction, 25 uL of microtubule/KSP solution was added to the ATP/compound mixture. The plates were incubated at room temperature for 1 hr. At the end of incubation period, 65 uL of Biomol Green was added to each well. The plates were incubated for 5-10 min and then the absorbance at 630 nm was determined. Biomol Green reagent is a malachite green based dye that detects the release of inorganic phosphate. Developed color signal was read using a Victor II reader. The concentration of each compound for 50% inhibition ($IC_{50}$) was calculated by nonlinear regression using either XLFit for Excel or Prism data analysis software by GraphPad Software Inc.

While the preferred embodiment of the invention has been illustrated and described, it will be appreciated that various changes can be made therein without departing from the spirit and scope of the invention.

What is claimed is:

1. A compound having the formula:

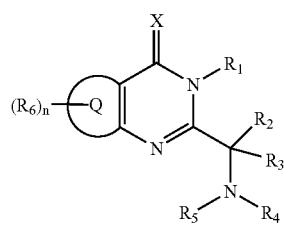

wherein Q is thienyl;
X is O or S;
$R_1$ is hydrogen, or substituted or unsubstituted alkyl, alkenyl, alkynyl, aryl, heteroaryl, heterocyclyl, alkylsulfonyl, or arylsulfonyl;
$R_2$ is hydrogen, or substituted or unsubstituted alkyl, alkenyl, alkynyl, aryl, heteroaryl, heterocyclyl, alkylsulfonyl, arylsulfonyl, alkylcarboxy, aminocarboxy, aminocarbonyl, or alkylsulfonamido; or $COR_7$, $CO_2R_7$, $CONR_8R_9$, $S(O)_mR_{10}$, or $SO_2NR_{11}R_{12}$;
$R_3$ is cyano, substituted or unsubstituted arylsulfonyl, or $CONR_8R_9$;
$R_4$ is hydrogen, or substituted or unsubstituted alkyl, alkenyl, alkynyl, aryl, heteroaryl, or heterocyclyl; or $L-R_{13}$, wherein L is a C1-C10 saturated or unsaturated branched or unbranched carbon chain comprising one or more methylene groups, wherein one or more methylene groups are optionally independently replaced by O, N, or S; and wherein L is optionally substituted with one or two oxo groups and one or more C1-C10 branched or unbranched alkyl optionally substituted by one or more halogen atoms;
$R_5$ is hydrogen, or substituted or unsubstituted alkyl, alkenyl, alkynyl, alkoxy, aryl, heteroaryl, or heterocyclyl; or $COR_7$, $CO_2R_7$, $CONR_8R_9$, or $SO_{(m)}R_{10}$;
$R_6$ is hydrogen, halogen, hydroxy, nitro, amino, cyano, alkoxy, alkylthio, methylenedioxy, or haloalkoxy; or substituted or unsubstituted alkyl, alkenyl, alkynyl, aryl, heteroaryl, alkylamino, dialkylamino, alkylsulfonyl, arylsulfonyl, alkylcarboxy, carboxyamino, carboxyamido, aminocarboxy, aminocarbonyl, or alkylsulfonamido;
$R_7$, $R_8$, $R_9$, $R_{10}$, $R_{11}$, and $R_{12}$ are independently selected from hydrogen, or substituted or unsubstituted alkyl, alkenyl, alkynyl, aryl, heteroaryl, or heterocyclyl; or $R_8$ and $R_9$, or $R_{11}$ and $R_{12}$ taken together form a 3- to 7-membered carbocyclic or heterocyclic ring;
$R_{13}$ is amino, alkylamino, or dialkylamino; or substituted or unsubstituted guanidino or heterocyclyl;
m=0, 1, or 2; and
n=0, 1, 2, or 3; or
the tautomers or pharmaceutically acceptable salts thereof.

2. A compound of claim 1, wherein substituted alkyl comprises arylalkyl, heteroarylalkyl, heterocyclyalkyl, aminoalkyl, alkylaminoalkyl, dialkyaminoalkyl, or sulfonamidoalkyl.

3. A compound of claim 1, wherein X is O.

4. A compound of claim 1, wherein $R_1$ is arylalkyl.

5. A compound of claim 1, wherein $R_1$ is benzyl.

6. A compound of claim 1, wherein $R_2$ is hydrogen and $R_3$ is $CONR_8R_9$.

7. A compound of claim 6, wherein $R_8$ and $R_9$ are independently selected from hydrogen, methyl, ethyl, or isopropyl.

8. A compound of claim 1, wherein $R_4$ is $L-R_{13}$.

9. A compound of claim 8, wherein $L-R_{13}$ is aminoalkyl.

10. A compound of claim 8, wherein $L-R_{13}$ is aminopropyl, alkylaminopropyl, or dialkylaminopropyl.

11. A compound of claim 8, wherein $L-R_{13}$ is aminopropyl.

12. A compound of claim 1, wherein $R_5$ is hydrogen, alkyl, aryl, or $COR_7$.

13. A compound of claim 1, wherein $R_5$ is $COR_7$.

14. A compound of claim 13, wherein $R_7$ is substituted or unsubstituted aryl or heteroaryl.

15. A compound of claim 13, wherein $R_7$ is alkyl- or halogen-substituted aryl.

16. A compound of claim 13 wherein $R_7$ is substituted or unsubstituted phenyl, pyridyl, or pyrazinyl.

17. A compound of claim 1, wherein $R_6$ is hydrogen, alkyl, chloro, or bromo.

18. A compound having the formula:

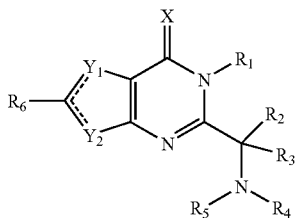

wherein X is O or S;
$Y_1$ is S and $Y_2$ is $CR_{15}$; or
$Y_1$ is $CR_{15}$ and $Y_2$ is S;
wherein, the dashed line represents a double bond to $Y_1$, when $Y_1$ is $CR_{15}$, and a double bond to $Y_2$, when $Y_2$ is $CR_{15}$;
$R_1$ is hydrogen, or substituted or unsubstituted alkyl, alkenyl, alkynyl, aryl, heteroaryl, heterocyclyl, alkylsulfonyl, or arylsulfonyl;
$R_2$ is hydrogen, or substituted or unsubstituted alkyl, alkenyl, alkynyl, aryl, heteroaryl, heterocyclyl, alkylsulfonyl, arylsulfonyl, alkylcarboxy, aminocarboxy, aminocarbonyl, or alkylsulfonamido; or $COR_7$, $CO_2R_7$, $CONR_8R_9$, $S(O)_mR_{10}$, or $SO_2NR_{11}R_{12}$;
$R_3$ is cyano, substituted or unsubstituted arylsulfonyl, or $CONR_8R_9$;
$R_4$ is hydrogen, or substituted or unsubstituted alkyl, alkenyl, alkynyl, aryl, heteroaryl, or heterocyclyl; or L-$R_{13}$, wherein L is a C1-C10 saturated or unsaturated branched or unbranched carbon chain comprising one or more methylene groups, wherein one or more methylene groups are optionally independently replaced by O, N, or S; and wherein L is optionally substituted with one or two oxo groups and one or more C1-C10 branched or unbranched alkyl optionally substituted by one or more halogen atoms;
$R_5$ is hydrogen, or substituted or unsubstituted alkyl, alkenyl, alkynyl, alkoxy, aryl, heteroaryl, or heterocyclyl; or $COR_7$, $CO_2R_7$, $CONR_8R_9$, or $SO_{(m)}R_{10}$;
$R_6$ is hydrogen, halogen, hydroxy, nitro, amino, cyano, alkoxy, alkylthio, methylenedioxy, or haloalkoxy; or substituted or unsubstituted alkyl, alkenyl, alkynyl, aryl, heteroaryl, alkylamino, dialkylamino, alkylsulfonyl, arylsulfonyl, alkylcarboxy, carboxyamino, carboxyamido, aminocarboxy, aminocarbonyl, or alkylsulfonamido;
$R_7$, $R_8$, $R_9$, $R_{10}$, $R_{11}$, and $R_{12}$ are independently selected from hydrogen, or substituted or unsubstituted alkyl, alkenyl, alkynyl, aryl, heteroaryl, or heterocyclyl; or $R_8$ and $R_9$, or $R_{11}$, and $R_{12}$ taken together form a 3- to 7-membered carbocyclic or heterocyclic ring;
$R_{13}$ is amino, alkylamino, or dialkylamino; or substituted or unsubstituted guanidino or heterocyclyl;
$R_{15}$ are independently selected from hydrogen, or substituted or unsubstituted alkyl, alkenyl, alkynyl, aryl, heteroaryl, or heterocyclyl;
m=0, 1, or 2; or
the tautomers, pharmaceutically acceptable salts, or prodrugs thereof.

19. A compound of claim 18, wherein substituted alkyl comprises arylalkyl, heteroarylalkyl, heterocyclyalkyl, aminoalkyl, alkylaminoalkyl, dialkyaminoalkyl, or sulfonamidoalkyl.

20. A compound of claim 18, wherein X is O.

21. A compound of claim 18, wherein $R_1$ is arylalkyl.

22. A compound of claim 18, wherein $R_1$ is benzyl.

23. A compound of claim 18, wherein $R_2$ is hydrogen and $R_3$ is $CONR_8R_9$.

24. A compound of claim 23, wherein $R_8$ and $R_9$ are independently selected from hydrogen, methyl, ethyl, or isopropyl.

25. A compound of claim 18, wherein $R_4$ is L-$R_{13}$.

26. A compound of claim 25, wherein L-$R_{13}$ is aminoalkyl.

27. A compound of claim 25, wherein L-$R_{13}$ is aminopropyl, alkylaminopropyl, or dialkylaminopropyl.

28. A compound of claim 25, wherein L-$R_{13}$ is aminopropyl.

29. A compound of claim 18, wherein $R_5$ is hydrogen, alkyl, aryl, or $COR_7$.

30. A compound of claim 18, wherein $R_5$ is $COR_7$.

31. A compound of claim 30, wherein $R_7$ is substituted or unsubstituted aryl or heteroaryl.

32. A compound of claim 30, wherein $R_7$ is alkyl- or halogen-substituted aryl.

33. A compound of claim 30, wherein $R_7$ is substituted or unsubstituted phenyl, pyridyl, or pyrazinyl.

34. A compound of claim 18, wherein $R_6$ is hydrogen, alkyl, chloro, or bromo.

35. A compound selected from:
N-(3-aminopropyl)-N-[1-(3-benzyl-6-bromo-4-oxo-3,4-dihydrothieno[3,2-d]pyrimidin-2-yl)-2-(dimethylamino)-2-oxoethyl]pyrazine-2-carboxamide;
N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-5-methylpyrazine-2-carboxamide;
N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-4-chlorobenzamide;
N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-6-methylnicotinamide;
N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-4-methylbenzamide; or
N-(3-aminopropyl)-N-[1-(3-benzyl-6-bromo-4-oxo-3,4-dihydrothieno[3,2-d]pyrimidin-2-yl)-2-(dimethylamino)-2-oxoethyl]-6-chloronicotinamide.

36. A composition, comprising a pharmaceutically acceptable carrier and an amount of a compound of claims 1, 18, or 35 effective to inhibit KSP (Kinesin Spindle Protien) activity in a human or animal subject when administered thereto.

37. The composition of claim 36 further comprising at least one additional agent for the treatment of cancer.

38. The composition of claim 37, wherein the additional agent for the treatment of cancer is selected from irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

39. A method for inhibiting KSP (Kinesin Spindle Protien) activity in a human or animal subject, comprising administering to the human or animal subject a composition comprising an amount of a compound of claims 1, 18, or 35 effective to inhibit KSP (Kinesin Spindle Protien) activity the human or animal subject.

40. A kit, comprising a compound of claims 1, 18, or 35 and a package insert or other labeling including directions for treating a cellular proliferative disease by administering an KSP (Kinesin Spindle Protien) inhibitory amount of the compound.

* * * * *

UNITED STATES PATENT AND TRADEMARK OFFICE
CERTIFICATE OF CORRECTION

PATENT NO. : 7,345,046 B2
APPLICATION NO. : 10/850429
DATED : March 18, 2008
INVENTOR(S) : W. Wang et al.

It is certified that error appears in the above-identified patent and that said Letters Patent is hereby corrected as shown below:

| COLUMN | LINE | ERROR |
|---|---|---|
| 41 (Claim 18, | 58 line 45 of text) | "are" should read --is-- |
| 41 (Claim 18, | 60 line 47 of text) | "heterocyclyl;" should read --heterocyclyl; and-- |
| 41 (Claim 18, | 62-63 lines 49-50 of text) | "the tautomers, pharmaceutically acceptable salts, or pro-drugs thereof." should read --the tautomers or pharmaceutically acceptable salts thereof.-- |
| 42 (Claim 36, | 54 line 3) | "Protien)" should read --Protein)-- |
| 42 (Claim 38, | 62 line 3) | delete "trastuzumab," |
| 42 (Claim 39, | 67 line 2) | "tien)" should read --tein)-- |
| 43 (Claim 39, | 3 line 5) | "Protien)" should read --Protein)-- |
| 43 (Claim 39, | 4 line 6) | "the human" should read --in the human-- |

UNITED STATES PATENT AND TRADEMARK OFFICE
CERTIFICATE OF CORRECTION

PATENT NO. : 7,345,046 B2
APPLICATION NO. : 10/850429
DATED : March 18, 2008
INVENTOR(S) : W. Wang et al.

It is certified that error appears in the above-identified patent and that said Letters Patent is hereby corrected as shown below:

| COLUMN | LINE | ERROR |
|---|---|---|
| 44 (Claim 40, | 2 line 4) | "Protien)" should read --Protein)-- |

Signed and Sealed this

Twenty-eighth Day of April, 2009

JOHN DOLL
*Acting Director of the United States Patent and Trademark Office*